(12) United States Patent
Weiner et al.

(10) Patent No.: US 9,278,128 B2
(45) Date of Patent: *Mar. 8, 2016

(54) VACCINES AND IMMUNOTHERAPEUTICS COMPRISING IL-15 RECEPTOR ALPHA AND/OR NUCLEIC ACID MOLECULES ENCODING THE SAME, AND METHODS FOR USING THE SAME

(71) Applicant: THE TRUSTEES OF THE UNIVERSITY OF PENNSYLVANIA, Philadelphia, PA (US)

(72) Inventors: David B. Weiner, Merion, PA (US); Kimberly A. Kraynyak, Blue Bell, PA (US); Michele Kutzler, Souderton, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 32 days.

This patent is subject to a terminal disclaimer.

(21) Appl. No.: 14/148,359

(22) Filed: Jan. 6, 2014

(65) Prior Publication Data

US 2014/0193439 A1    Jul. 10, 2014

Related U.S. Application Data

(63) Continuation of application No. 13/391,615, filed as application No. PCT/US2010/048827 on Sep. 14, 2010, now Pat. No. 8,624,011.

(60) Provisional application No. 61/242,210, filed on Sep. 14, 2009.

(51) Int. Cl.
  *A61K 39/00*    (2006.01)
  *A61K 39/39*    (2006.01)
  *A61K 39/21*    (2006.01)
  (Continued)

(52) U.S. Cl.
  CPC .................. *A61K 39/39* (2013.01); *A61K 39/00* (2013.01); *A61K 39/12* (2013.01); *A61K 39/21* (2013.01); *C07K 14/7155* (2013.01); *A61K 2039/53* (2013.01); *A61K 2039/55516* (2013.01);
  (Continued)

(58) Field of Classification Search
  None
  See application file for complete search history.

(56) References Cited

U.S. PATENT DOCUMENTS

| 4,722,848 A | 2/1988 | Paoletti et al. |
| 4,945,050 A | 7/1990 | Sanford et al. |

(Continued)

FOREIGN PATENT DOCUMENTS

| WO | WO 2007084342 A2 * | 7/2007 |
| WO | 2008014521 | 1/2008 |

(Continued)

OTHER PUBLICATIONS

Gen Bank Accession No. AAP69528.1 (2003).*

(Continued)

*Primary Examiner* — Benjamin P Blumel
*Assistant Examiner* — M. Franco Salvoza
(74) *Attorney, Agent, or Firm* — Riverside Law LLP

(57) ABSTRACT

Compositions, recombinant vaccines and live attenuated pathogens comprising one or more isolated nucleic acid molecules that encode an immunogen in combination with an isolated nucleic acid molecule that encodes IL-15Ra or a functional fragment thereof are disclosed. Methods of inducing an immune response in an individual against an immunogen, using such compositions are disclosed.

2 Claims, 15 Drawing Sheets

(51) Int. Cl.
  *C07K 14/715* (2006.01)
  *A61K 39/12* (2006.01)
(52) U.S. Cl.
  CPC ............ *A61K2039/55527* (2013.01); *C12N 2740/16234* (2013.01)

(56) References Cited

U.S. PATENT DOCUMENTS

| | | | |
|---|---|---|---|
| 5,017,487 | A | 5/1991 | Stunnenberg et al. |
| 5,036,006 | A | 7/1991 | Sanford et al. |
| 5,077,044 | A | 12/1991 | Stocker |
| 5,110,587 | A | 5/1992 | Paoletti et al. |
| 5,112,749 | A | 5/1992 | Brey, III et al. |
| 5,174,993 | A | 12/1992 | Paoletti |
| 5,223,424 | A | 6/1993 | Cochran et al. |
| 5,225,336 | A | 7/1993 | Paoletti |
| 5,240,703 | A | 8/1993 | Cochran |
| 5,242,829 | A | 9/1993 | Panicalli et al. |
| 5,273,525 | A | 12/1993 | Hofmann |
| 5,294,441 | A | 3/1994 | Curtiss, III |
| 5,294,548 | A | 3/1994 | McLinden et al. |
| 5,310,668 | A | 5/1994 | Ellis et al. |
| 5,387,744 | A | 2/1995 | Curtiss, III et al. |
| 5,389,368 | A | 2/1995 | Curtiss, III |
| 5,424,065 | A | 6/1995 | Curtiss, III et al. |
| 5,439,440 | A | 8/1995 | Hofmann |
| 5,451,499 | A | 9/1995 | Cochran |
| 5,453,364 | A | 9/1995 | Paoletti |
| 5,462,734 | A | 10/1995 | Letchworth, III et al. |
| 5,470,734 | A | 11/1995 | Sondermeijer et al. |
| 5,482,713 | A | 1/1996 | Paoletti |
| 5,580,859 | A | 12/1996 | Felgner et al. |
| 5,593,972 | A | 1/1997 | Weiner et al. |
| 5,676,594 | A | 10/1997 | Joosten |
| 5,702,359 | A | 12/1997 | Hofmann et al. |
| 5,703,055 | A | 12/1997 | Felgner et al. |
| 5,739,118 | A | 4/1998 | Carrano et al. |
| 5,739,972 | A | 4/1998 | Smith et al. |
| 5,810,762 | A | 9/1998 | Hofmann |
| 5,817,637 | A | 10/1998 | Weiner et al. |
| 5,830,876 | A | 11/1998 | Weiner et al. |
| 5,962,428 | A | 10/1999 | Carrano et al. |
| 5,981,505 | A | 11/1999 | Weiner et al. |
| 5,993,434 | A | 11/1999 | Dev et al. |
| 6,014,584 | A | 1/2000 | Hofmann et al. |
| 6,055,453 | A | 4/2000 | Hofmann et al. |
| 6,068,650 | A | 5/2000 | Hofmann et al. |
| 6,110,161 | A | 8/2000 | Mathiesen et al. |
| 6,120,493 | A | 9/2000 | Hofmann |
| 6,135,990 | A | 10/2000 | Heller et al. |
| 6,181,964 | B1 | 1/2001 | Hofmann et al. |
| 6,216,034 | B1 | 4/2001 | Hofmann et al. |
| 6,233,482 | B1 | 5/2001 | Hofmann et al. |
| 6,241,701 | B1 | 6/2001 | Hofmann |
| 6,347,247 | B1 | 2/2002 | Dev et al. |
| 6,418,341 | B1 | 7/2002 | Hofmann et al. |
| 6,451,002 | B1 | 9/2002 | Dev et al. |
| 6,516,223 | B2 | 2/2003 | Hofmann |
| 6,567,694 | B2 | 5/2003 | Hayakawa |
| 6,610,044 | B2 | 8/2003 | Mathiesen |
| 6,654,636 | B1 | 11/2003 | Dev et al. |
| 6,678,556 | B1 | 1/2004 | Nolan et al. |
| 6,697,669 | B2 | 2/2004 | Dev et al. |
| 6,763,264 | B2 | 7/2004 | Hofmann |
| 6,778,853 | B1 | 8/2004 | Heller et al. |
| 6,865,416 | B2 | 3/2005 | Dev et al. |
| 6,939,862 | B2 | 9/2005 | Bureau et al. |
| 6,958,060 | B2 | 10/2005 | Mathiesen et al. |
| 7,005,498 | B1* | 2/2006 | Steinaa et al. .......... 530/324 |
| 2006/0263857 | A1 | 11/2006 | Lefrancois et al. |
| 2007/0041941 | A1 | 2/2007 | Weiner et al. |
| 2007/0104686 | A1 | 5/2007 | Weiner et al. |
| 2007/0160578 | A1* | 7/2007 | Waldmann et al. ........ 424/85.2 |
| 2008/0255039 | A1* | 10/2008 | Bernard et al. ........... 514/12 |
| 2009/0227664 | A1 | 9/2009 | Pavlakis et al. |
| 2009/0238791 | A1* | 9/2009 | Jacques et al. ........... 424/85.2 |

FOREIGN PATENT DOCUMENTS

| | | |
|---|---|---|
| WO | 2008138017 | 11/2008 |
| WO | 2009002562 | 12/2008 |
| WO | 2009007244 | 1/2009 |

OTHER PUBLICATIONS

Yan et al. "Induction of antitumor immunity in vivo following delivery of a novel HPV-16 vaccine encoding an E6/E7 fusion antigen," Vaccine 27: 431-440 (2009).*
Dubois, S. et al., "IL-15Ralpha recycles and presents IL-15 in trans to neighboring cells", Immunity, 2002, 17:537-547.
Koka, R. et all, "Cutting edge: murine dendritic cells require IL-15R alpha to prime NK cells", J Immunol, 2004, 173:3594-3598.
Lucas et al., "Dendritic cells prime natural killer cells by trans-presenting interleukin 15", Immunity, 2007 26:503-517.
Sato et al., "The IL-15/IL-15Ralpha on cell surfaces enables sustained IL-15 activity and contributes to the long survival of CD8 memory T cells", Proc Natl Acad Sci U S A. Jan. 9, 2007;104(2):588-93.
Duitman, E. H., et al., "How a cytokine is chaperoned through the secretory pathway by complexing with its own receptor lessons from IL-15/IL-15R (alpha)", Mol Cell Biol, Aug. 2008, 28(15):4851-61.
Lodolce et al., "IL-15 receptor maintains lymphoid homeostasis by supporting lymphocyte homing and proliferation", Immunity, 1998, 9(5):669-76.
Lodolce et al., "T Cell—Independent Interleukin 15rα Signals Are Required for Bystander Proliferation", J Exp Med. 2001, 194(8): 1187-1194.
Burkett, P.R. et al., "Coordinate expression and trans presentation of interleukin (IL)-15 alpha and IL-15 supports natural killer cell and memory CDS+ T cells homeostatis", The Journal of Experimental Medicine, 2004, 200:825-834.
Schluns KS et al., "Transregulation of memory CD8 T-cell proliferation by IL-15Ralpha+ bone marrow-derived cells", Blood, 2004, 103:988-994.
Bergamaschi, C. et al., "Intracellular interaction of interleukin-15 with its receptor alpha during production leads to mutual stabilization and increased bioactivity", The Journal of Biological Chemistry, 2008, 283:4189-4199.
Oh et al., "Coadministration of HIV vaccine vectors with vaccinia viruses expressing IL-15 but not IL-2 induces long-lasting cellular immunity", Proc Natl Acad Sci U S A. Mar. 18, 2003;100(6):3392-7.
Kutzler, M.A. et al., "Coimmunization with an optimized IL-15 plasmid results in enhanced function and longevity of CDS T cells that are partially independent of CD4 T cell help", J Immunol, 2005, 175:112-123.
Zhang et al., "Coimmunization with IL-15 plasmid enhances the longevity of CD8 T cells induced by DNA encoding hepatitis B virus core antigen" World J Gastroenterol, Aug. 7, 2006, 12(29):4727-35.
Calarota, S.A., "IL-15 as memory T-cell adjuvant for topical HIV-1 DermaVir vaccine", Vaccine, Sep. 19, 2008, 26 (40):5188-95.
Li et al., "Efficient augmentation of a long-lasting immune responses in HIV-1 gag DNA vaccination by IL-15 plasmid boosting", Vaccine, Jun. 19, 2008, 26(26):3282-90.
Burkett, P.R. et al., "IL-15R alpha expression on CDS+ T cells is dispensable forT cell memory", Proc. Natl. Acad. Sci., 2003, 100:4724-4729.
Schluns et al., "Distinct cell types control lymphoid subset development by means of IL-15 and IL-15 receptor alpha expression" Proc Natl Acad Sci U S A, Apr. 13, 2004;101(15):5616-212.
Sandau et al., "Cutting edge: transpresentation of IL-15 by bone marrow-derived cells necessitates expression of IL-15 and IL-15R alpha by the same cells", J Immunol. Dec. 1, 2004;173(11):6537-41.
Genbank accession No. NM172200.
Genbank accession No. NM002189.
Genbank accession No. Q13261.
Genbank accession No. NP002180.

(56) References Cited

OTHER PUBLICATIONS

Genbank accession No. NP751950.
Genbank accession No. NM172174.
Genbank accession No. NM000585.
Genbank accession No. CAA86100.
Genbank accession No. CAA62616.
Genbank accession No. AA 100964.
Genbank accession No. CAA72044.
Genbank accession No. AAH18149.
Genbank accession No. AAU21241.
Kim et al., "CD8 positive T cells influence antigen-specific immune responses through the expression of chemokines", J Clin Invest, Sep. 15, 1998, 102(6):1112-24.
Kennedy, M.K. et al., "Reversible defects in natural killer and memory CDS T cell lineages in interleukin 15-deficient mice", The Journal of Experimental Medicine, 2000, 191:771-780.
Anderson et al., "Chromosomal assignment and genomic structure of Il15", Genomics, Feb. 10, 1995, 25(3):701-6.
Anderson et al., "Functional characterization of the human interleukin-15 receptor alpha chain and close linkage of IL15RA and IL2RA genes", The Journal of Biological Chemistry, 1995, 270:29862-29869.
Becker, T.C. et al., "Interleukin 15 is required for proliferative renewal of virus-specific memory CDS T cells", The Journal of Experimental Medicine, 2002, 195: 1541-154S.
Boyer, J.D. et al., "Protection against simian/human immunodeficiency virus (SHIV) S9.6P in macaques after coimmunization with SHIV antigen and IL-15 plasmid", Proc. Natl. Acad. Sci., 2007, 104:18648-18653.
Bulanova, E. et al., "The IL-15R alpha chain signals through association with Syk in human B cells". J Immunol, 2001, 167:6292-6302 (article retracted Feb. 15, 2011).
Giri, J.G. et al., "Utilization of the beta and gamma chains of the IL-2 receptor by the novel cytokine IL-15", The EMBO Journal, 1994, 13:2822-2830.
Giri, J.G. et al., "IL-15, a novel T cell growth factor that shares activities and receptor components with IL-2", Journal of Leukocyte Biology, 1995, 57:763-766.
Khan, A.S. et al., Optimization of electroporation parameters for the intramuscular delivery of plasmids in pigs, DNA and Cell Biology, 2003, 22:807-814.
Leifert et al., "Targeting plasmid-encoded proteins to the antigen presentation pathways", Immunol Rev, Jun. 2004;199:40-53.
Oh et al., "IL-15/IL-15Ralpha-mediated avidity maturation of memory CD8+ T cells", Proc Natl Acad Sci U S A, Oct. 19, 2004, 101(42):15154-9.
Oh et al., "IL-15 as a mediator of CD4+ help for CD8+ T cell longevity and avoidance of TRAIL-mediated apoptosis", Proc Natl Acad Sci U S A, Apr. 1, 2008, 105(13):5201-6.
Laddy et al., "Heterosubtypic protection against pathogenic human and avian influenza viruses via in vivo electroporation of synthetic consensus DNA antigens", PLoS One, Jun. 25, 2008, 3(6):e2517.
Kraynyak et al., "Plasmid-encoded interleukin-15 receptor alpha enhances specific immune responses induced by a DNA vaccine in vivo", Human Gene Therapy, 2009, 20(10):1143-1156.
Jalah et al., "Efficient systemic expression of bioactive IL-15 in mice upon delivery of optimized DNA expression plasmids", DNA and Cell Biology, 2007, 26(12):827-840.
Garmory et al., "DNA Vaccines: Improving Expression of Antigens", Genetic Vaccines and Therapy, 2003, 1(2):1-5.
Ferko et al., "Live attenuated influenza 9-12 virus expressing human interleukin-2 reveals increased immunogenic potential in young and aged hosts", Journal of Virology, 2006, 80(23):11621-11627.
K.C. Ngumbela et al., "Quantitative Effect of Suboptimal Codon Usage on Translational Efficiency of mRNA Encoding HIV-1 gag in Intact T Cells", PLoS ONE, 2003, 3(6):1-5.

* cited by examiner

VACCINES AND IMMUNOTHERAPEUTICS COMPRISING IL-15 RECEPTOR ALPHA AND/OR NUCLEIC ACID MOLECULES ENCODING THE SAME, AND METHODS FOR USING THE SAME

CROSS-REFERENCE TO RELATED APPLICATIONS

This application is a continuation of U.S. patent application Ser. No. 13/391,615, filed Jun. 7, 2012, which issued on Jan. 7, 2014 as U.S. Pat. No. 8,624,011, which claims priority to and is a United States National Stage filing under 35 USC §371 of International PCT Application Serial No. PCT/US2010/048827, filed Sep. 14, 2010, which claims priority to U.S. Provisional Application No. 61/242,210, filed Sep. 14, 2009, each of which is incorporated herein by reference in its entirety.

FIELD OF THE INVENTION

The present invention relates to improved vaccines, improved methods for prophylactically and/or therapeutically immunizing individuals against immunogens, and to improved immunotherapeutic compositions and improved immunotherapy methods.

BACKGROUND OF THE INVENTION

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response in such cases, the immunotherapeutic increases the immune response and/or selectively enhances a portion of the immune response (such as the cellular arm or the humoral arm) which is desirable to treat or prevent the particular condition, infection or disease.

Vaccine protocols can be improved by the delivery of agents that modulate a person's immune responses to induce an improved immune response. In some vaccination protocols in which the individual is administered a vaccine that exposes the individual to an immunogen against which the individual generates an immune response, an agent is provided that increases the immune response and/or selectively enhances a portion of the immune response (such as the cellular arm or the humoral arm) which is desirable to treat or prevent the particular condition, infection or disease.

Vaccines are useful to immunize individuals against target antigens such as allergens, pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines that produce the target antigen in cells of the vaccinated individual are effective in inducing the cellular arm of the immune system. Specifically, live attenuated vaccines, recombinant vaccines which use avirulent vectors, and DNA vaccines each lead to the production of antigens in the cell of the vaccinated individual which results in induction of the cellular arm of the immune system. On the other hand, killed or inactivated vaccines, and sub-unit vaccines which comprise only proteins do not induce good cellular immune responses although they do induce an effective humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

The generation of potent CD8+ T cell responses by DNA vaccine technology is a goal sought by DNA vaccine developers. There are reports that CD8+ T cells contribute to controlling viral replication in both human (Koup et al., 1994; Cao et al., 1995; Musey et al., 1997; Ogg et al., 1998; Betts et al., 1999) and non human primate models (Jin et al., 1999; Schmitz et al., 1999; Barouch et al., 2000; Amara et al., 2001; Shiver et al., 2002) in the HIV model as well as other viral infections.

Many different strategies have been used along with DNA vaccine technology, including improved delivery techniques, enhanced construct design, heterologous prime-boost strategies, and the use of molecular adjuvants. Molecular adjuvants including chemokines and cytokines can be incorporated into a vaccine strategy to skew the immune response towards cellular or humoral immunity. Cytokines such as IL-12 and IL-15 have been effective in enhancing the immune response in both murine and non-human primate models (Morrow and Weiner, 2008).

Interleukin-15 (IL-15) has been shown to play a role in the generation and maintenance of CD8+ T cells as it signals through the common βγ chain, which is also utilized by IL-2. IL-15 has been shown to be trans-presented on the surface of antigen presenting cells via IL-15Rα during the priming of Natural Killer and CD8+T cells (Dubois et al., 2002; Koka et al., 2004; Lucas et al., 2007; Sato et al., 2007). IL-15Rα has also recently been shown to play a role in the regulation of IL-15 secretion (Duitman et al., 2008). This cell surface complex is thought to allow IL-15 to signal thorough the βγ receptor on memory CD8+ T cells promoting cell division and survival of these cells (Lodolce et al., 1998; Kennedy et al., 2000; Lodolce et al., 2001; Burkett et al., 2003; Burkett et al., 2004; Sandau et al., 2004; Schluns et al., 2004a; Schluns et al., 2004b). IL-15 and IL-15Rα together as a complex exhibit enhanced stability and secretion compared to either molecule alone (Bergamaschi et al., 2008).

In regards to its employment in vaccination models, the use of plasmid-encoded IL-15 as an HIV-1 vaccine adjuvant has been previously reported to enhance cytolytic and memory CD8+T cell responses in mice (Oh et al., 2003; Kutzler et al., 2005; Zhang et al., 2006; Calarota et al., 2008; Li et al., 2008). Studies in rhesus macaques have also shown the ability of IL-15 to enhance effector functions of CD4+T cells (Picker et al., 2006) and rescued dual IFN-γ/TNF responses in both effector CD4+ and CD8+ T cells (Halwani et al., 2008). Importantly, addition of pIL-15 with SIV/HIV antigens in rhesus macaques resulted in enhanced protection after SHIV89.6p challenge (Boyer et al., 2007).

While such vaccines are often effective to immunize individuals prophylactically or therapeutically against pathogen infection or human diseases, there is a need for improved vaccines. There is a need for compositions and methods that produce an enhanced immune response. There still remains a need for improved strategies to enable effective DNA vaccines, including new adjuvants that enhance the immune response to DNA vaccines.

Likewise, while some immunotherapeutics are useful to modulate immune response in a patient there remains a need for improved immunotherapeutic compositions and methods.

SUMMARY OF THE INVENTION

The present invention relates to nucleic acid molecules that comprise SEQ ID NO: 1 or fragments thereof that encode proteins with IL-15Ra immunomodulatory function and/or IL-15 binding function and/or binding function to other subunits of a IL-15 receptor complex.

The present invention relates to a composition an isolated nucleic acid molecule that encodes an immunogen in combination with an isolated nucleic acid molecule that encodes or IL-15Ra or functional fragments thereof.

The present invention further relates to a composition an isolated nucleic acid molecule that encodes both an immunogen and IL-15Ra or functional fragments thereof.

The present invention relates to injectable pharmaceutical compositions comprising an isolated nucleic acid molecule that encodes an immunogen in combination with an isolated nucleic acid molecule that encodes IL-15Ra or functional fragments thereof.

The present invention relates to injectable pharmaceutical compositions comprising an isolated nucleic acid molecule that encodes both an immunogen and IL-Ra or functional fragments thereof.

In some aspects of the invention, the immunogen is a pathogen antigen, a cancer-associated antigen or an antigen from cells associated with autoimmune disease. In some aspects the pathogen is a pathogen that causes chronic infection.

The present invention further relates to methods of inducing an immune response in an individual against an immunogen, comprising administering to the individual a composition an isolated nucleic acid molecule that encodes an immunogen in combination with an isolated nucleic acid molecule that encodes IL-15Ra or functional fragments thereof.

The present invention further relates to methods of inducing an immune response in an individual against an immunogen, comprising administering to the individual a nucleic acid molecule that encodes an immunogen and IL-15Ra or functional fragments thereof.

The present invention further relates to recombinant vaccines comprising a nucleotide sequence that encodes an immunogen operably linked to regulatory elements, a nucleotide sequences that encode IL-15Ra or functional fragments thereof, and to methods of inducing an immune response in an individual against an immunogen comprising administering such a recombinant vaccine to an individual.

The present invention further relates to a live attenuated pathogen, comprising a nucleotide sequence that encodes IL-15Ra or functional fragments thereof, and to methods of inducing an immune response in an individual against a pathogen comprising administering the live attenuated pathogen to an individual.

BRIEF DESCRIPTION OF THE FIGURES

FIG. 1A shows Coomassie staining of the recombinant human IL-15Rα protein in 2-fold dilutions from 12.0 to 0.16 µg of protein. FIG. 1B shows that a commercial anti-human IL-15Rα antibody can detect recombinant IL-15Rα protein in a direct ELISA. FIG. 1C shows the immunization schedule for anti-human IL-15Rα monoclonal antibody generation in BALB/c mice. FIG. 1D shows that hybridoma supernatants from Clone KK1.23 have high titers of antibody against recombinant IL-15Rα protein by ELISA. FIG. 1E shows that the purified monoclonal antibody KK1.23 binds recombinant IL-15Rα in ELISA and specifically as shown by Western blot analysis.

FIG. 2A depicts how human IL-15Rα cDNA was inserted into a pVAX1 expression vector. FIGS. 2B and 2C show that plasmid IL-15Rα expresses the appropriate size protein (~30 kDa) as detected by radioactive in vitro translation with the R&D and the KK1.23 monoclonal anti-human IL-15Rα antibody, respectively. FIG. 2D shows that monoclonal KK1.23 antibody (IgG1 isotype) does not bind non-transfected HeLa cells (20×). FIG. 2E shows pTRACER-IL-15Rα transfected cells (green) stained with a mouse IgG1 isotype control (20×). FIGS. 2F and 2G show that the KK1.23 anti-human IL-15Rα antibody (red) binds pIL-15Rα-pTRACER transfected cells at 20× and at 60×, respectively.

FIG. 3A shows the immunization schedule for groups of BALB/c mice that were injected with DNA formulations containing combinations of vector, antigenic plasmid (HIV-1 gag and pol), pIL-15, and/or pIL-15Rα. The combination of pIL-15/pIL-15Rα was either given in the same leg or split between two different legs (pIL-15 in one, pIL-15Rα in another). Intramuscular immunizations were given with electroporation 3 times, and mice were sacrificed one week following the final boost. FIGS. 3B and 3C show cellular responses. Splenocytes from immunized mice were used in an IFN-γ ELISpot assay. Splenocytes were stimulated overnight with medium (negative control), Concanavalin A (positive control) or antigenic peptide (HIV-1 gag and pol pools) and IFN-γ spot forming units were counted.

FIG. 5A shows the total antigenic response for whole splenoctyes (black bars) and CD8 depleted splenocytes (gray bars) and was measured by IFN-γ ELISpot. In FIG. 5B, antibody titers against HIV-1 gag p24 antigenic protein were determined from sera samples of BALB/c mice immunized with the same constructs and timeline as described in the materials and methods. Dilutions of sera taken at the time of sacrifice were run on an ELISA plate coated with p24 and detected with an anti-mouse IgG-HRP antibody to measure levels of antigen specific IgG. Background responses in diluent wells only were subtracted from the sample OD values before graphing.

FIG. 6A shows IFN-γ secretion was measured from splenocytes of immunized mice by IFN-γ ELISpot. FIG. 6B shows intracellular cytokine staining used to determine the memory response from immunized mice. Splenocytes from immunized mice were stimulated for 5 hours with medium, PMA/Ionomycin, or the dominant and subdominant HIV-1 gag and pol antigenic peptides in the presence of Brefeldin A. In FIG. 6C, sera was taken from immunized mice and run on an HIV-1 gag p24 ELISA. Dilutions of sera were analyzed for antigen specific IgG. Background responses in diluent wells only were subtracted from the sample OD values before graphing.

FIG. 7A shows radiolabeled human IL-15Rα binds mouse IL-15 and is co-immunoprecipitated with anti-mouse IL-15 antibody. Immunizations were also repeated in control C57BL/6, shown in FIG. 7B, and IL-15 knockout mice, shown in FIG. 7C, according to the schedule in FIG. 3A and IFN-γ ELISpots were performed on splenocytes.

DETAILED DESCRIPTION OF PREFERRED EMBODIMENTS

Figure 1A:
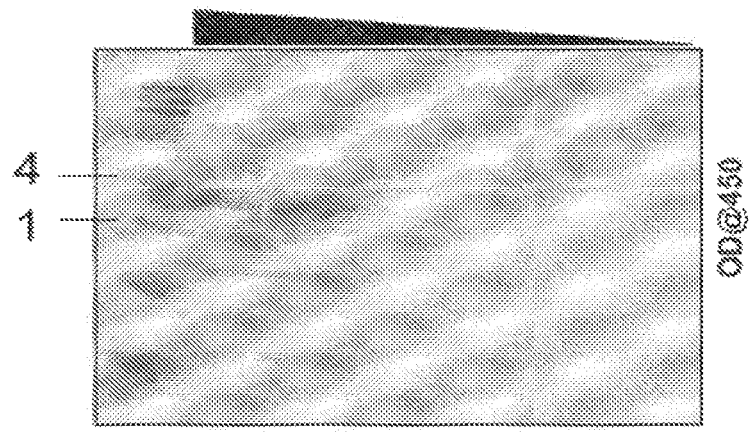
FIGS. 1A-1E show results and information related to the generation of an IL-15Rα monoclonal antibody.

As used herein, the term "IL-15Ra" refers to interleukin 15 receptor alpha protein.

As used herein, "functional fragment" is meant to refer to a fragment of IL-15Ra that, when delivered in conjunction with an immunogen, provides an increased immune response compared to the immune that is induced when the immunogen is delivered without the fragment. Fragments are generally 10 or more amino acids in length.

As used herein the term "target protein" is meant to refer to peptides and protein encoded by gene constructs of the present invention that act as target proteins for an immune response. The terms "target protein" and "immunogen" are used interchangeably and refer to a protein against which an immune response can be elicited. The target protein is an immunogenic protein that shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated.

As used herein, the term "genetic construct" refers to the DNA or RNA molecules that comprise a nucleotide sequence which encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs that contain the necessary regulatory elements operably linked to a coding sequence that encodes a target protein or an immunomodulating protein, such that when present in the cell of the individual, the coding sequence will be expressed.

As used herein, the term "sharing an epitope" refers to proteins that comprise at least one epitope that is identical to or substantially similar to an epitope of another protein.

As used herein, the term "substantially similar epitope" is meant to refer to an epitope that has a structure that is not identical to an epitope of a protein but nonetheless invokes a cellular or humoral immune response that cross-reacts to that protein.

As used herein, the term "intracellular pathogen" is meant to refer to a virus or pathogenic organism that, at least part of its reproductive or life cycle, exists within a host cell and therein produces or causes to be produced, pathogen proteins.

As used herein, the term "hyperproliferative diseases" is meant to refer to those diseases and disorders characterized by hyperproliferation of cells.

As used herein, the term "hyperproliferative-associated protein" is meant to refer to proteins that are associated with a hyperproliferative disease.

The invention arises from the discovery that when delivered as part of a vaccine, nucleic acid molecules that encode IL-15Ra and functional fragments thereof, and combinations thereof modulate immune responses. Accordingly nucleic acid molecules that encode IL-15Ra and functional fragments thereof, and combinations thereof may be delivered as immunotherapeutics in combination with or as components of a vaccine.

Additionally, the invention arises from the discovery that when delivered as part of a vaccine, nucleic acid molecules that encode IL-15Ra or functional fragments thereof, in combination with nucleic acid molecules that IL-15 or functional fragments thereof modulate immune responses. Accordingly nucleic acid molecules that encode IL-15Ra or functional fragments thereof, in combination with nucleic acid molecules that IL-15 or functional fragments may be delivered as immunotherapeutics in combination with or as components of a vaccine.

Some aspects of the invention provide the use of nucleic acid coding sequences of IL-15Ra protein in therapeutic vaccines, particularly in such cases where a CD8+ memory T cell response is not desired. Such therapeutic vaccines include those in which the antigen target is an antigen expressed in normal as well as disease associated cells whereby short term elimination of antigen-bearing cells has a therapeutic effect without a long term immune response directed to normal cells expressing the antigen. Accordingly, this aspect of the invention is particularly useful in therapeutic vaccines directed toward antigens on cancer cells which are also present on normal cells, therapeutic vaccines directed toward antigens expressed by cells associated with autoimmune disease which are also present on normal cells, and therapeutic vaccines directed toward pathogen antigens involved in chronic infections for which a persistent immune response would be undesirable. Chronic infections refer to those pathogen infections in which the pathogen is not cleared. Examples include but are not limited to HCV, HSV, CMV, chicken pox, HIV, and the like, as contrasted with acute infections such as polio, small pox, mumps and the like.

Some aspects of the invention provide the use of nucleic acid coding sequences that encodes IL-15Ra protein in combination with nucleic acid coding sequences that encodes IL-15 in therapeutic vaccines, particularly in such cases where an enhanced burst immune response is desired. The combination of nucleic acid coding sequences of IL-15Ra protein and nucleic acid coding sequences that encodes IL-15 provide an additive adjuvant effect upon initial induction of the immune response. The nucleic acid coding sequences that encodes IL-15Ra protein may be administered to the same site as the nucleic acid coding sequences that encodes IL-15 or the nucleic acid coding sequences that encodes IL-15Ra protein and the nucleic acid coding sequences may be delivered to different sites to achieve the additive immune response.

The nucleotide sequence of human IL-15Ra is disclosed as Genbank accession nos. NM172200 and NM002189, which are each incorporated herein by reference. The protein sequence of human IL-15Ra is disclosed as Genbank accession nos. Q13261, NP002180 and NP751950, which are each incorporated herein by reference. In some embodiments of the invention, a nucleic acid coding sequences that encodes IL-15Ra protein is optimized for high levels of expression. In some embodiments of the invention, a nucleic acid coding sequences that encodes IL-15Ra protein are optimized such as in SEQ ID NO:1. In some embodiments of the invention, nucleic acid coding sequences that encodes IL-15Ra protein are non-optimized such as in SEQ ID NO:2.

The nucleotide sequence of human IL-15 is disclosed as Genbank accession nos. NM172174 and NM000585, which are each incorporated herein by reference. The protein sequence of human IL-15 is disclosed as Genbank accession nos. CAA86100, CAA62616, AAI00964, CAA72044, AAH18149 and AAU21241, which are each incorporated herein by reference. In some embodiments of the invention, a nucleic acid coding sequences that encodes IL-15 protein is optimized for high levels of expression. In some embodiments, improved IL-15 constructs such as those described in U.S. Ser. No. 10/560,650 (US 20070041941), which is incorporated herein by reference, are used. In some embodiments, improved IL-15 constructs such as those described in U.S. Ser. No. 12/160,766, which is incorporated herein by reference, are used. In some embodiments of the invention, a nucleic acid coding sequences that encodes IL-15 protein is SEQ ID NO:3.

In some embodiments of the invention, the nucleic acid coding sequences that encodes IL-15Ra protein and the nucleic acid coding sequence that encodes the target antigen are each on the same plasmid.

In some embodiments of the invention, a composition is provided comprising two plasmids: a first plasmid comprising the nucleic acid coding sequences that encodes IL-15Ra protein; and a second plasmid comprising the nucleic acid coding sequence that encodes the target antigen are each on the same plasmid.

In some embodiments of the invention, two compositions are provided. The first composition comprises a plasmid comprising the nucleic acid coding sequences that encodes IL-15Ra protein, and the second composition comprises a plasmid comprising the nucleic acid coding sequence that encodes the target antigen are each on the same plasmid. The two compositions may be provided in separate containers and packaged as a kit.

In some embodiments of the invention, the nucleic acid coding sequences that encodes IL-15Ra protein, the nucleic acid coding sequences that encodes IL-15, and the nucleic acid coding sequence that encodes the target antigen are each on the same plasmid. In some embodiments of the invention, the invention provides a composition that comprises two plasmids. The nucleic acid coding sequences that encodes IL-15Ra protein and the nucleic acid coding sequences that encodes IL-15 are on one plasmid and the nucleic acid coding sequence that encodes the target antigen on a second plasmid.

In some embodiments of the invention, the invention provides a composition that comprises three plasmids. The nucleic acid coding sequence that encodes IL-15Ra protein is on a first plasmid, the nucleic acid coding sequence that encodes IL-15 is on a second plasmid and the nucleic acid coding sequence that encodes the target antigen on a third plasmid.

In some embodiments of the invention, the invention provides two compositions, a first composition that comprises one plasmid and a second composition that comprises one plasmid. In some such embodiments, the first composition comprises a plasmid that comprises the nucleic acid coding sequence that encodes IL-15Ra protein and the nucleic acid coding sequence that encodes the target antigen. The second composition comprises a plasmid that comprises the nucleic acid coding sequences that encodes IL-15. In some such embodiments, the first composition comprises a plasmid that comprises the nucleic acid coding sequence that encodes IL-15 protein and the nucleic acid coding sequence that encodes the target antigen. The second composition comprises a plasmid that comprises the nucleic acid coding sequences that encodes IL-15Ra. In some such embodiments, the first composition comprises a plasmid that comprises the nucleic acid coding sequence that encodes IL-15 protein and the nucleic acid coding sequence that encodes IL-15Ra. The second composition comprises a plasmid that comprises the nucleic acid coding sequences that encodes the target antigen. The multiple compositions may be provided in separate containers that are packaged to form a kit.

In some embodiments of the invention, the invention provides two compositions, a first composition that comprises two plasmids and a second composition that comprises one plasmid. In some such embodiments, the first composition comprises a first plasmid that comprises the nucleic acid coding sequence that encodes IL-15Ra protein and a second plasmid that comprises the nucleic acid coding sequence that encodes the target antigen. The second composition comprises a plasmid that comprises the nucleic acid coding sequences that encodes IL-15. In some such embodiments, the first composition comprises a first plasmid that comprises the nucleic acid coding sequence that encodes IL-15 protein and a second plasmid that comprises the nucleic acid coding sequence that encodes the target antigen. The second composition comprises a plasmid that comprises the nucleic acid coding sequences that encodes IL-15Ra. In some such embodiments, the first composition comprises a first plasmid that comprises the nucleic acid coding sequence that encodes IL-15 protein and a second plasmid that comprises the nucleic acid coding sequence that encodes IL-15Ra. The second composition comprises a plasmid that comprises the nucleic acid coding sequences that encodes the target antigen. The multiple compositions may be provided in separate containers that are packaged to form a kit.

In some embodiments of the invention, the invention provides three compositions, a first composition that comprises one plasmid, a second composition that comprises one plasmid and a third composition that comprises one plasmid. In some such embodiments, the first composition comprises a plasmid that comprises the nucleic acid coding sequence that encodes IL-15Ra protein. The second composition comprises a plasmid that comprises the nucleic acid coding sequence that encodes the target antigen. The third composition comprises a plasmid that comprises the nucleic acid coding sequences that encodes IL-15. The multiple compositions may be provided in separate containers that are packaged to form a kit.

Isolated cDNA that encodes the immunomodulating proteins are useful as a starting material in the construction of constructs that can produce that immunomodulating protein. Using standard techniques and readily available starting materials, a nucleic acid molecule that encodes an immunomodulating protein may be prepared.

The nucleic acid molecules may be delivered using any of several well known technologies including DNA injection (also referred to as DNA vaccination), recombinant vectors such as recombinant adenovirus, recombinant adenovirus associated virus and recombinant vaccinia virus.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gene guns".

Another route of administration involves the use of electroporation to deliver the genetic construct, as described in U.S. Pat. Nos. 5,273,525, 5,439,440, 5,702,359, 5,810,762, 5,993,434, 6,014,584, 6,055,453, 6,068,650, 6,110,161, 6,120,493, 6,135,990, 6,181,964, 6,216,034, 6,233,482, 6,241,701, 6,347,247, 6,418,341, 6,451,002, 6,516,223, 6,567,694, 6,569,149, 6,610,044, 6,654,636, 6,678,556, 6,697,669, 6,763,264, 6,778,853, 6,865,416, 6,939,862 and 6,958,060, which are hereby incorporated by reference.

When taken up by a cell, the genetic constructs) may remain present in the cell as a functioning extrachromosomal molecule. DNA may be introduced into cells, where it is present on a transient basis, in the form of a plasmid or plasmids. Alternatively, RNA may be administered to the cell. It is also contemplated to provide the genetic construct as a linear minichromosome including a centromere, telomeres and an origin of replication. Gene constructs may constitute part of the genetic material in attenuated live microorganisms or recombinant microbial vectors which are administered to subjects. Gene constructs may be part of genomes of recombinant viral vaccines where the genetic material remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operably linked to the sequence that encodes the desired proteins and that the regulatory elements are operable in the individual to whom they are administered.

An initiation codon and a stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals, bovine growth hormone polyadenylation (bgh-PolyA) signal and LTR polyadenylation signals. In particular, the SV40 polyadenylation signal that is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as alpha-interferon, gamma-interferon, platelet derived growth factor (PDGF), TNF, GM-CSF, epidermal growth factor (EGF), IL-1, IL-2, IL-4, IL-6, IL-10, IL-12 and IL-15 including IL-15 having the signal sequence deleted and optionally including the signal peptide from IgE.

The compositions used in the methods may further comprise one or more of the following proteins and/or nucleic acid molecules encoding such proteins, as set forth in U.S. Ser. No. 10/139,423, which corresponds to U.S. Publication No. 20030176378, which is incorporated herein by reference: Major Histocompatibility Complex antigens including Major Histocompatibility Complex Class I antigen or Major Histocompatibility Complex Class II antigen; death domain receptors including, but not limited to, Apo-1, Fas, TNFR-1, p55, WSL-1, DR3, TRAMP, Apo-3, AIR, LARD, NGRF, DR4, DR5, KILLER, TRAIL-R2, TRICK2, and DR6; death signals, i.e. proteins that interact with the death domain receptors including, but not limited to FADD, FAP-1, TRADD, RIP, FLICE, and RAIDD; or death signals that include ligands that bind death domain receptors and initiate apoptosis including, but not limited to, FAS-L, and TNF; and mediators that interact with death domain receptors including, but not limited to, FADD, MORT1, and MyD88; toxins including proteins which kill cells such as, but not limited to, insect and snake venoms, bacterial endotoxins such as Psuedomoneus endotoxin, double chain ribosome inactivating proteins such as ricin including single chain toxin, and gelonin.

The compositions used in the methods may further comprise one or more of the following proteins and/or nucleic acid molecules encoding such proteins, as set forth in U.S. Ser. No. 10/560,650, which corresponds to U.S. Publication No. 20070041941, which is incorporated herein by reference: IL-15 including fusion proteins comprising non-IL-15 signal peptide linked to IL-15 protein sequences such as fusion proteins comprising an IgE signal peptide linked to IL-15 protein sequences, CD40L, TRAIL; TRAILrecDRC5, TRAIL-R2, TRAIL-R3, TRAIL-R4, RANK, RANK LIGAND, Ox40, Ox40 LIGAND, NKG2D, F461811 or MICA, MICB, NKG2A, NKG2B, NKG2C, NKG2E, NKG2F, CD30, CD153 (CD30L), Fos, c-jun, Sp-1, Ap1, Ap-2, p38, p65Rel, MyD88, IRAK, TRAF6, IkB, NIK, SAP K, SAP1, JNK2, JNK1B2, JNK1B1, JNK2B2, JNK2B1, JNK1A2, JNK2A1, JNK3A1, JNK3A2, NF-kappa-B2, p49 splice form, NF-kappa-B2, p100 splice form, NF-kappa-B2, p105 splice form, NF-kappa-B 50K chain precursor, NFkB p50, human IL-1.alpha., human IL-2, human IL-4, murine IL-4, human IL-5, human IL-10, human IL-15, human IL-18, human TNF-.alpha., human TNF-.beta., human interleukin 12, MadCAM-1, NGF IL-7, VEGF, TNF-R, Fas, CD40L, IL-4, CSF, G-CSF, GM-CSF, M-CSF, LFA-3, ICAM-3, ICAM-2, ICAM-1, PECAM, PI50.95, Mac-1, LFA-1, CD34, RANTES, IL-8, MIP-1.alpha., E-selecton, CD2, MCP-1, L-selecton, P-selecton, FLT, Apo-1, Fas, TNFR-1, p55, WSL-1, DR3, TRAMP, Apo-3, AIR, LARD, NGRF, DR4 (TRAIL), DR5, KILLER, TRAIL-R2, TRICK2, DR6, ICE, VLA-1, and CD86 (B7.2).

The compositions used in the methods may further comprise one or more of the following proteins and/or nucleic acid molecules encoding such proteins, as set forth in U.S. Ser. No. 10/560,653, which corresponds to U.S. Publication No. 20070104686, which is incorporated herein by reference: Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, and TAP2.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

In some embodiments, gene constructs may be provided to in order to produce coding sequences for the immunomodulatory proteins described herein linked to IgE signal peptide.

One method of the present invention comprises the steps of administering nucleic acid molecules intramuscularly, intranasally, intraperitoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Pat. Nos. 5,593,972 and 5,962,428, which are each incorporated herein by reference. Genetic vaccine facilitator agents are described in U.S. Pat. No. 5,739,118, which is incorporated herein by reference. The co-agents that are administered in conjunction with nucleic acid molecules may be administered as a mixture with the nucleic acid molecule or administered separately simultaneously, before or after administration of nucleic-acid molecules. In addition, other agents which may function transfecting agents and/or replicating agents and/or inflammatory agents and which may be co-administered with a polynucleotide function enhancer include growth factors, cytokines and lymphokines such as a-interferon, gamma-interferon, GM-CSF, platelet derived growth factor (PDGF), TNF, epidermal growth factor (EGF), IL-1, IL-2, IL-4, IL-6, IL-10, IL-12 and IL-15 as well as fibroblast growth factor, surface active agents such as immune-stimulating complexes (ISCOMS), LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a polynucleotide function enhancer. In some embodiments, the nucleic acid molecule is provided in association with poly(lactide-co-glycolide) (PLG), to enhance delivery/uptake.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some embodiments of the invention, methods of inducing immune responses against an immunogen are provided by delivering a combination of the immunogen and IL-15Rα or functional fragments thereof to an individual. The vaccine may be a live attenuated vaccine, a recombinant vaccine or a nucleic acid or DNA vaccine.

The present invention is useful to elicit enhanced immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to some aspects of the present invention, DNA or RNA that encodes a target protein and immunomodulating protein is introduced into the cells of tissue of an individual where it is expressed, thus producing the encoded proteins. The DNA or RNA sequences encoding the target protein and immunomodulating protein are linked to regulatory elements necessary for expression in the cells of the individual. Regulatory elements for DNA expression include a promoter and a polyadenylation signal. In addition, other elements, such as a Kozak region, may also be included in the genetic construct.

In some embodiments, expressible forms of sequences that encode the target protein and expressible forms of sequences that encode both immunomodulating proteins are found on the same nucleic acid molecule that is delivered to the individual.

In some embodiments, expressible forms of sequences that encode the target protein occur on a separate nucleic acid molecule from expressible forms of sequences that encode the immunomodulatory protein. In some embodiments, expressible forms of sequences that encode the target protein and expressible forms of sequences that encode one or more of the immunomodulatory proteins occur on a one nucleic acid molecule that is separate from the nucleic acid molecule that contain expressible forms of sequences that encode the immunomodulating protein]. Multiple different nucleic acid molecules can be produced and delivered according to the present invention.

The nucleic acid molecule(s) may be provided as plasmid DNA, the nucleic acid molecules of recombinant vectors or as part of the genetic material provided in an attenuated vaccine. Alternatively, in some embodiments, the target protein and immunomodulating protein may be delivered as a protein in addition to the nucleic acid molecules that encode them or instead of the nucleic acid molecules which encode them.

Genetic constructs may comprise a nucleotide sequence that encodes a target protein or an immunomodulating protein operably linked to regulatory elements needed for gene expression. According to the invention, combinations of gene constructs that include one construct that comprises an expressible form of the nucleotide sequence that encodes a target protein and one construct that includes an expressible form of the nucleotide sequence that encodes an immunomodulating protein are provided. Delivery into a living cell of the DNA or RNA molecule(s) that include the combination of gene constructs results in the expression of the DNA or RNA and production of the target protein and one or more immunomodulating proteins. An enhanced immune response against the target protein results.

The present invention may be used to immunize an individual against pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, *listeria* and *shigella*. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2. Those skilled in the art can readily identify and distinguish those pathogens which cause chronic infections from those which are cleared post infection, i.e. acute infection.

TABLES

TABLE 1

Viruses

Picornavirus Family
    Genera:
        Rhinoviruses: (Medical) responsible for ~50% cases of the common cold.
        Etheroviruses: (Medical) includes polioviruses, coxsackieviruses, echoviruses, and human enteroviruses such as hepatitis A virus.
        Apthoviruses: (Veterinary) these are the foot and mouth disease viruses.
        Target antigens: VP1, VP2, VP3, VP4, VPG
Calcivirus Family
    Genera:
        Norwalk Group of Viruses: (Medical) these viruses are an important causative agent of epidemic gastroenteritis.
Togavirus Family
    Genera:
        Alphaviruses: (Medical and Veterinary) examples include Sindbis virus, RossRiver virus and Venezuelan Eastern & Western Equine encephalitis viruses.
        Reovirus: (Medical) Rubella virus.
Flariviridae Family
    Examples include: (Medical) dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541)
        Representative Target antigens: E NS5 C
Hepatitis C Virus: (Medical) these viruses are not placed in a family yet but are believed to be either a togavirus or a flavivirus. Most similarity is with togavirus family.
Coronavirus Family: (Medical and Veterinary)
    Infectious bronchitis virus (poultry)
    Porcine transmissible gastroenteric virus (pig)

TABLE 1-continued

| Viruses |
|---|

Porcine hemagglutinating encephalomyelitis virus (pig)
Feline infectious peritonitis virus (cats)
Feline enteric coronavirus (cat)
Canine coronavirus (dog)
SARS associated coronavirus
The human respiratory coronaviruses cause about 40% of cases of common cold. EX. 224E, OC43 Note - coronaviruses may cause non-A, B or C hepatitis
Target antigens: E1 - also called M or matrix protein E2 - also called S or Spike protein E3 - also called BE or hemagglutin-elterose glycoprotein (not present in all coronaviruses) N - nucleocapsid
Rhabdovirus Family
    Genera:
    Vesiculovirus, Lyssavirus: (medical and veterinary) rabies;
    Target antigen: G protein, N protein
Filoviridae Family: (Medical)
    Hemorrhagic fever viruses such as Marburg and Ebola virus
Paramyxovirus Family:
    Genera:
    Paramyxovirus: (Medical and Veterinary) Mumps virus, New Castle disease virus (important pathogen in chickens)
        Morbillivirus: (Medical and Veterinary) Measles, canine distemper
        Pneumovirus: (Medical and Veterinary) Respiratory syncytial virus
Orthomyxovirus Family (Medical) The Influenza virus
Bunyavirus Family
    Genera:
    Bunyavirus: (Medical) California encephalitis, La Crosse
    Phlebovirus: (Medical) Rift Valley Fever
    Hantavirus: Puremala is a hemahagin fever virus
    Nairvirus (Veterinary) Nairobi sheep disease
    Also many unassigned bungaviruses
Arenavirus Family (Medical) LCM, Lassa fever virus
Reovirus Family
    Genera:
    Reovirus: a possible human pathogen
    Rotavirus: acute gastroenteritis in children
    Orbiviruses: (Medical and Veterinary) Colorado Tick fever,
    Lebombo (humans) equine encephalosis, blue tongue
Retroyirus Family
    Sub-Family:
    Oncorivirinal: (Veterinary) (Medical) feline leukemia virus, HTLVI and HTLVII
    Lentivirinal: (Medical and Veterinary) HIV, feline immunodeficiency virus, equine infections, anemia virus
Spumavirinal Papovavirus Family
    Sub-Family: Polyomaviruses: (Medical) BKU and JCU viruses
    Sub-Family: Papillomavirus: (Medical) many viral types associated with cancers or malignant progression of papilloma.
        Adenovirus (Medical) EX AD7, ARD., O.B. - cause respiratory disease - some adenoviruses such as 275 cause enteritis
Parvovirus Family (Veterinary)
    Feline parvovirus: causes feline enteritis
    Feline panleucopeniavirus
    Canine parvovirus
    Porcine parvovirus
Herpesvirus Family
    Sub-Family:
    alphaherpesviridue
    Genera:
    Simplexvirus (Medical)
    HSVI (Genbank X14112, NC001806),
    HSVII (NC001798)
    Varicella zoster: (Medical Veterinary)
    Pseudorabies
    varicella zoster
    Sub-Family
    betaherpesviridae
    Genera:
    Cytomegalovirus (Medical)
    HCMV
    Muromegalovirus
    Sub-Family.
    Gammaherpesviridae
    Genera:
    Lymphocryptovirus (Medical)
    EBV - (Burkitt's lymphoma)
Poxvirus Family
    Sub-Family:
    Chordopoxviridae (Medical - Veterinary)
    Genera:

TABLE 1-continued

Viruses

*Variola* (Smallpox)
*Vaccinia* (Cowpox)
Parapoxivirus - Veterinary
Auipoxvirus - Veterinary
Capripoxvirus
Leporipoxvirus
Suipoxviru's
Sub-Family:
Entemopoxviridue
Hepadnavirus Family
    Hepatitis B virus
    Unclassified Hepatitis delta virus

TABLE 2

Bacterial pathogens
    Pathogenic gram-positive cocci include: pneumococcal; staphylococcal; and streptococcal.
    Pathogenic gram-negative cocci include: meningococcal; and gonococcal.
    Pathogenic enteric gram-negative bacilli include: *enterobacteriaceae; pseudomonas*, acinetobacteria and *eikenella* , melioidosis; *salmonella* ; shigellosis; *haemophilus*; chancroid; brucellosis; tularemia; *yersinia (pasteurella)*; *streptobacillus mortiliformis* and spirillum; *listeria monocytogenes; erysipelothrix rhusiopathiae*; diphtheria, cholera, anthrax; donovanosis (*granuloma inguinale*); and bartonellosis.
    Pathogenic anaerobic bacteria include: tetanus; botulism; other clostridia; tuberculosis; leprosy; and other mycobacteria.
    Pathogenic spirochetal diseases include: syphilis; - treponematoses: yaws, pinta and endemic syphilis; and leptospirosis.
    Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and chromomycosis; and dermatophytosis.
    Rickettsial infections include rickettsial and rickettsioses.
    Examples of mycoplasma and chlamydial infections include: *mycoplasma pneumoniae; lymphogranuloma venereum*; psittacosis; and perinatal chlamydial infections.
    Pathogenic eukaryotes
    Pathogenic protozoans and helminths and infections thereby include: amebiasis; malaria; leishmaniasis; trypanosomiasis; toxoplasmosis; *pneumocystis carinii*; babesiosis; giardiasis; trichinosis; filariasis; schistosomiasis; nematodes; trematodes or flukes; and cestode (tapeworm) infections.

In order to produce a genetic vaccine to protect against pathogen infection, genetic material that encodes immunogenic proteins against which a protective immune response can be mounted must be included in a genetic construct as the coding sequence for the target. Because DNA and RNA are both relatively small and can be produced relatively easily, the present invention provides the additional advantage of allowing for vaccination with multiple pathogen antigens. The genetic construct used in the genetic vaccine can include genetic material that encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against human immunodeficiency virus (HIV), herpes simplex virus (HSV), hepatitis C virus (HCV), West Nile Virus (WNV) or hepatitis B virus (HBV).

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. To immunize against hyperproliferative diseases, a genetic construct that includes a nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anticancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) that are involved in the disease have been characterized. These TCRs include V.beta.-3, V.beta.-14, 20 V.beta.-17 and Va-17. Thus, vaccination with a DNA construct that encodes at least one of these proteins will elicit an immune response that will target T cells involved in RA. See: Howell, M. D., et al., 1991 Proc. Nat. Acad. Sci. USA 88:10921-10925; Piliard, X., et al, 1991 Science 253:325-329; Williams, W. V., et al., 1992 J Clin. Invest. 90:326-333; each of which is incorporated herein by reference. In MS, several specific variable regions of TCRs that are involved in the disease have been characterized. These TCRs include VfP and Va-10. Thus, vaccination with a DNA construct that encodes at least one of these proteins will elicit an immune response that will target T cells involved in MS. See: Wucherpfennig, K. W., et al., 1990 Science 248:1016-1019; Oksenberg, J. R., et al, 1990 Nature 345:344-346; each of which is incorporated herein by reference.

In scleroderma, several specific variable regions of TCRs that are involved in the disease have been characterized. These TCRs include V.beta.-6, V.beta.-8, V.beta.-14 and Va-16, Va-3C, Va-7, Va-14, Va-15, Va-16, Va-28 and Va-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al 1987 Sequence of Proteins of Immunological Interest U.S. Department of Health and Human Services, Bethesda Md., which is incorporated herein by reference. In addition, a general method for cloning functional variable regions from antibodies can be found in Chaudhary, V. K., et al, 1990 Proc. Natl. Acad Sci. USA 87:1066, which is incorporated herein by reference.

In addition to using expressible forms of immunomodulating protein coding sequences to improve genetic vaccines, the present invention relates to improved attenuated live vaccines and improved vaccines that use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence that encodes an IL-R15α or functional fragments thereof, wherein the nucleotide sequence is operably linked to regulatory sequences that can function in the vaccine to effect expression. The gene constructs are incorporated in the attenuated live vaccines and recombinant vaccines to produce improved vaccines according to the invention.

The present invention provides an improved method of immunizing individuals that comprises the step of delivering gene constructs to the cells of individuals as part of vaccine compositions which include DNA vaccines, attenuated live vaccines and recombinant vaccines. The gene constructs comprise a nucleotide sequence that encodes an IL-15 RECEPTOR ALPHA or functional fragments and that is operably linked to regulatory sequences that can function in the vaccine to effect expression. The improved vaccines result in an enhanced cellular immune response.

EXAMPLE

Mice were co-immunized with pIL-15 and pIL-15Rα to determine enhanced immune response generated using HIV-1 DNA vaccine antigens. Data show that although the IL-15 and IL-15Rα combination indeed enhanced the overall cellular immune response, surprisingly the IL-15Rα plasmid augmented immune responses in an IL-15 independent manner. Importantly, the induced memory response was only maintained in mice co-vaccinated with pIL-15 as well as the pIL-15Rα, but not the IL-15Rα alone. These studies for the first time demonstrate that the IL-15Rα protein alone can function as an adjuvant with a limited immune expansion phenotype.

MATERIALS AND METHODS

Western Blot Analysis

Western blotting analysis was performed according to standard protocols. 3 μg per well of recombinant IL-15Rα or VPR protein (Abgent) was run on a SDS-PAGE gel (Cambrex, Rockland, Me.), blotted on nitrocellulose membrane, and probed with either the R&D or the KK1.23 anti-human IL-15Rα antibody. The signal was amplified using an anti-mouse IgG-HRP (Zymed) and detected with ECL (GE Healthcare, Chalfont St. Giles, United Kingdom).

DNA Plasmids

DNA vaccine constructs expressing HIV-1gag and HIV-1pol (Kim et al., 1998) and human IL-15 (Kutzler et al., 2005) were prepared as previously described. The open reading frame of human IL-15Rα was moved into pVAX1 and pTRACER vectors (Invitrogen, Carlsbad, Calif.). Restriction enzyme digestion using EcoRI and BamHI or NheI and EcoRI (New England Biolabs, Beverly, Mass.) were used, respectively. Positive clones were verified by sequence analysis.

In-Vitro Translation Assay

The TNT-T7 Quick Coupled Transcription/Translation Reticulocyte Lysate system (Promega, Wis.) and [35S] methionine were used to create labeled IL-15Rα protein product. pVAX vector alone (negative control) or pVAX vector containing IL-15Rα and [35S] methionine were added to the reaction mix according to the instructions supplied by the manufacturer. The reaction was carried out at 30° C. for 1 hour. Labeled proteins were immunoprecipitated using 5 μg purified monoclonal anti-IL-15Rα antibody (R&D Systems) or Clone KK1.23 at 4° C. with rotation overnight in RIPA buffer. Approximately 5 mg of protein G-Sepharose beads (GE Healthcare) (50 μL of 100 mg/mL stock) was added to each immunoprecipitation reaction, and the samples were incubated at 4° C. with rotation for 2 hours. The beads were washed three times with binding buffer containing high salt and bovine serum albumin and finally suspended in 2× sample buffer. The immunoprecipitated protein complexes were eluted from sepharose beads by boiling for 5 minutes and were run on a 12% SDS-PAGE gel (Cambrex). The gel was fixed and treated with amplifying solution (GE Healthcare), and dried for 2 hours in a gel drier (Bio-Rad, Hercules, Calif.). The dried gel was exposed to X-ray film at −80° and developed using the Kodak automatic developer (Kodak, Rochester, N.Y.).

Indirect Immunofluorescent Assay

The indirect immunofluorescent assay for confirmation of the pIL-15Rα plasmid expression was conducted by the following protocol previously described (Ramanathan et al., 2002). HeLa cells (ATCC, Rockville, Md.) grown in slide chambers (BD Biosciences, Bedford, Mass.) at a density of 100,000 cells per chamber in complete DMEM plus 10% FBS (Hyclone, Logan, Utah) and antibiotic-antimycotic (GIBCO, Invitrogen, Carlsbad, Calif.) were allowed to adhere overnight. Cells were transfected with pIL-15RαpTRACERor pVAX-1 (1 μg/well) using FuGENE 6 Transfection Reagent (Roche Diagnostics, Basel, Switzerland) according to manufacturer's protocol. Twenty-four hours after transfection, cells were washed with PBS and fixed on slides using 2% PFA/PBS for 1 hour at RT. Slides were incubated with 5 ug Clone KK1.23 mouse antihuman IL-15Rα made in our laboratory or IgG1 Isotype control (R&D systems, Minneapolis, Minn.) for 90 minutes at 37 degrees. Anti mouse IgG-Rhodamine conjugated secondary antibody (Santa Cruz Biotechnology, Santa Cruz, Calif.) was added at 1:200 and the slides were incubated for 45 minutes at RT. Following, DAPI (Molecular Probes, Invitrogen) stain for 10 minutes at RT, slides were mounted in Fluoromount G medium (Electron Microscopy Sciences, Hatfield, Pa.) and analyzed using the Phase 3 Image Pro Program for fluorescent microscopy (Media Cybernetics, Bethesda, Md.).

Plasmid Immunization and Mice

The tibialis anterior muscle of 6 to 8 week old female BALB/c (Jackson Laboratory, Bar Harbor, Me.), C57BL/6 (Taconic, Germantown, N.Y.), or IL-15 knockout (Taconic) (Kennedy et al., 2000) mice were injected 3 times, 2 weeks apart, and electroporated as previously described (Khan et al., 2003; Laddy et al., 2008) using the CELLECTRA® adaptive constant current device (VGX Pharmaceuticals, The Woodlands, Tex.). For all experiments in mice, the animals were immunized with either 35 ug of pVAX1, 5 μg of HIV-1 antigenic plasmid (gag, pol), 10 μg of pIL-15, and/or 7.5, 10, or 15 μg of pIL-15Rα (n=3-7 per group). Co-administration of various gene plasmids involved mixing the designated DNA plasmids before injection in 0.25% bupivicaine-HCL (Sigma) in isotonic citrate buffer (Kim et al., 1998; Kutzler et al., 2005) to a final volume of 40 μl. All animals were housed in a temperature-controlled, light-cycled facility at the University of Pennsylvania, and their care was under the guidelines of the National Institutes of Health and the University of Pennsylvania.

Method for Mouse Sacrifice, Sample Collection and Tissue Harvest

At timepoints designated in the immunization schedule, the animals were sedated using an analgesic and blood, was taken before animals were sacrificed by cervical dislocation. The spleen from each mouse were harvested and pooled (per experimental group) into a 15 ml conical containing R10 medium (RPMI1640 plus 10% fetal bovine serum, antibiotic/antimycotic, and B-Mercaptoethanol). In a sterile tissue culture hood, the pooled spleen/medium mixture from each experimental group was crushed into a single cell suspension using a stomacher apparatus (Seward 80, Metrohm, Riverview, Fla.). The cell/tissue stroma were put through a 40-micron cell strainer and washed with R10, pelleted and incubated for 5 minutes at room temperature in ACK lysing buffer (Lonza, Switzerland) to lyse red blood cells. The splenocytes were then counted and utilized in immune assays described below.

IFN-γ ELISPOT Assay

IFN-γ ELISPOT was performed as previously described (Kutzler et al., 2005) to determine antigen specific cytokine secretion from immunized mice. Briefly, ELISpot 96-well plates are coated with anti-mouse IFN-γ capture antibody and incubated for 24 hours at 4° C. (R&D Systems). 2×105 splenocytes from immunized mice were added to each well of an ELISpot plate and stimulated overnight at 37° C., 5% CO2, in the presence of R10 (negative control), concanavalin A (positive control), or specific peptide (HIV-1 gag or pol) antigens (10 ng/ml). HIV-1 Consensus Clade B subtype HIV-1 gag and pol 15-mer peptides spanning the entire respective protein, overlapping by 11 amino acids, were acquired from by the AIDS Reagent and Reference Repository (Frederick, Md.). For CD8 depletion experiments, CD8+ T cells were removed from total splenocytes by positive magnetic selection using an anti-CD8a (Ly-2) antibody (Miltenyi Biotech, Germany) according to manufacture's protocol. Following 24 hours of stimulation, the plates were washed and incubated at 4° C. overnight with biotinylated anti-mouse IFN-γ antibody (R&D Systems). The plates were washed and incubated with streptavidinalkaline phosphatase (R&D Systems) for 2 hours at room temperature. The plate was washed, and 5-Bromo-4-Chloro-3' Indolylphosphate p-Toluidine Salt (BCIP) and Nitro Blue Tetrazololium Chloride (NBT) (the Chromogen Color Reagent, R&D Systems) was added. The plate was rinsed with distilled water, and dried at room temperature. Spots were counted by an automated ELISpot reader (CTL Limited, Inc. Cleveland, Ohio). Raw values are determined and multiplied by a factor of five so that data is represented as spot forming cells per million splenocytes. Background values in the R10 wells of each group were subtracted from peptide-stimulated wells before graphing.

Intracellular Cytokine Staining HIV-1 specific T cell responses were also determined by intracellular cytokine staining using the Cytofix/Cytoperm Kit and standard protocol (BD Biosciences). Splenocytes from immunized mice were stimulated for 5 hours in the presence of 1 µl/ml Golgi-Plug (BD Biosciences) with R10 and DMSO (negative control), 10 ng/ml PMA and 250 ng/ml ionomycin (positive control), or HIV-1 consensus Clade B gag or pol 15-mer peptides. Prior to surface staining, cells were stained with the LIVE/DEAD fixable violet kit (Molecular Probes, Invitrogen) at 37° for 10 minutes and Fc block (BD) was added for 15 minutes at 4° to block Fc receptors. All antibodies were purchased from BD Biosciences and used at 1 ul/test. Prior to permeabilization/fixation cells were stained with CD4-Alexa700 and CD8-PerCP for 30 minutes at 4°. CD3-PECy5 and IFN-γ PE-Cy7 were included in the intracellular stain for 45 minutes at 4°. Data from 50,000 live CD3+ lymphocyte gated events were acquired using a LSRII flow cytometer (BD Biosciences) and analyzed using FlowJo software (Treestar, Inc., Ashland, Oreg.). Responses from the negative control wells were subtracted from the antigenic stimulations prior to graphing.

Analysis of HIV-1Gag Binding Antibodies

ELISA was used to determine HIV-1 Gag-specific antibodies IgG in mouse sera as described (Ogawa et al., 1989; Mestecky et al., 2004). EIA/RIA plates (Corning Costar, Cambridge, Mass.) were coated with 1 µg/ml of recombinant HIV-HUB gag p24 (Immunodiagnostics, Woburn, Mass.) diluted in PBS (Mediatech, Herndon, Va.) at a final volume of 100 ul per well and incubated overnight at 4 C. Plates were washed with PBS/Tween (0.05% Tween 20) and blocked against non-specific binding with 200 µl of blocking buffer/diluent (3% BSA in PBS) for 2 hours at room temperature. The plates were washed and dilutions of pooled sera from immunized mice were added in triplicate (100 µl per well), at dilutions from 1 to 10 to 1 to 1600 and incubated at room temperature for 2 hours. Bound antibodies were detected with horseradish peroxidase-labeled goat anti-mouse IgG (H+L) (Zymed) and developed with substrate TMB H2O2 (Sigma-Aldrich). The color reaction was stopped with 2N H2SO4, and the absorbance at 450 nm read in an EL312 Bio-Kinetics microplate reader (Bio-Tek Instruments Inc., Winooski, Vt.).

RESULTS

Generation of Anti-Human IL-15Rα Antibody

A monoclonal antibody was generated against human IL-15Rα, as commercially available antibodies are deficient in the ability to detect expression of the IL-15Rα plasmid (pIL-15Rα) on cells. Recombinant human IL-15Rα was generated as follows:

Recombinant human IL-15Rα protein was generated by Abgent (San Diego, Calif.). The open reading frame of human IL-15Rα (a generous gift from Thomas Waldmann (NCI, NIH, Bethesda, Md.)) was cloned into high expressing bacterial vector, pET21a (EMD Biosciences, Gibbstown, N.J.). Competent cells were transformed, amplified in E. coli, and recombinant protein was purified using a Ni-NTA column. The accuracy of the purified protein was confirmed by direct ELISA using anti-human IL-15Rα antibody (R&D Systems, Minneapolis, Minn.).

Figure 1B:
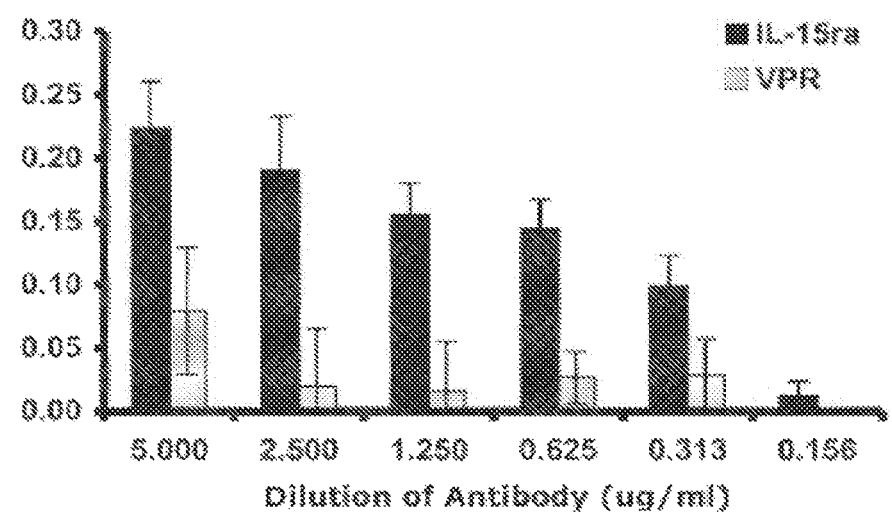

To confirm the size of the newly generated IL-15Rα protein, decreasing dilutions of purified protein were run on a SDS-PAGE gel and stained with coomassie blue dye (FIG. 1A). As shown in FIG. 1A, the generated protein runs at approximately 30 kDa, the expected size. This protein was tested for the ability to bind to commercially available antibody as an indication of its correct integrity. FIG. 1B shows an ELISA assay with plates captured with recombinant IL-15Rα or VPR protein, a negative control. VPR was used as it was produced by a similar method to the IL-15Rα protein. FIG. 1B shows that the commercially available anti-human IL-15Rα antibody can detect the generated recombinant protein.

Figure 1C:
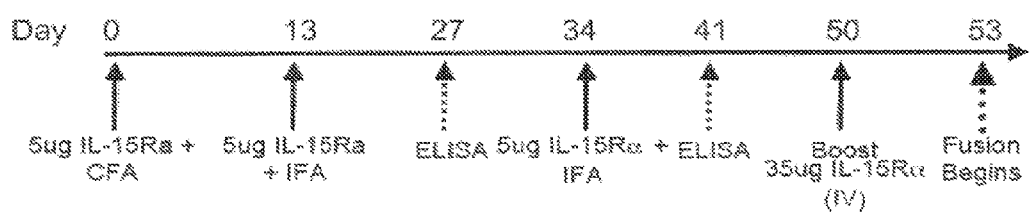

To generate an antibody against IL-15Rα, recombinant human IL-15Rα protein was injected into BALB/c mice as in FIG. 1C, and as follows:

Recombinant human IL-15Rα protein was injected into BALB/c mice (n=4) for monoclonal antibody generation. 5 µg of total protein emulsified in complete Freund's adjuvant (first immunization only) or incomplete Freund's adjuvant (subsequent immunizations) was given per injection (Sigma, St. Louis, Mo.). 50 µl was injected subcutaneously into each flank and 100 µl was injected into the peritoneum. Mice were given a final boost of 35 ug protein in sterile PBS intravenously three days prior to fusion. Antibody levels in the sera were determined by direct ELISA using recombinant IL-15Rα protein and anti-mouse IgG-HRP (Zymed, San Francisco, Calif.). One mouse with a 1:8,000 titer of antibody against IL-15Rα was sacrificed at its spleen removed for fusion with a myeloma cell line. 1,500 hybridoma supernatants were screened by ELISA, 8 positive clones were expanded, and one was purified by an ammonium sulfate column, antibody KK1.23. Monoclonal antibodies were generated and purified by Julia Conicello of the Wistar Institute Hybridoma Facility (Philadelphia, Pa.).

Figure 1D:
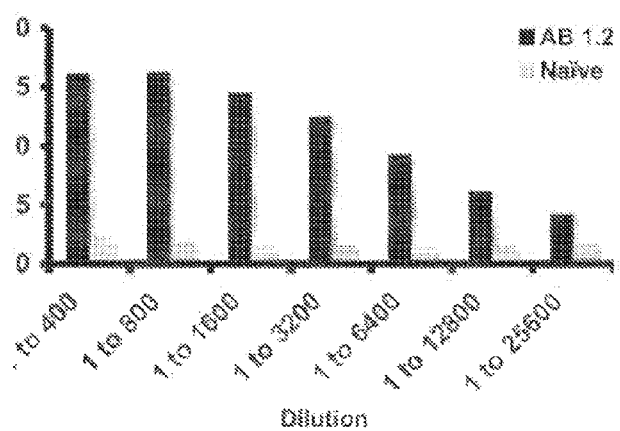
Figure 1E:
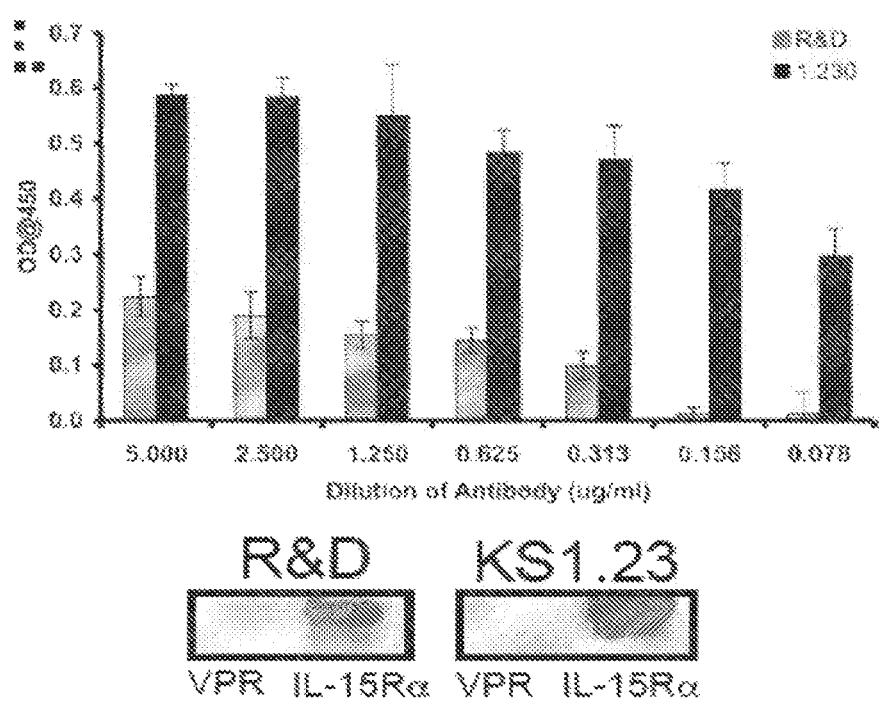

After screening approximately 1,500 hybridoma supernatants by ELISA, one hybridoma KK1.23 exhibited titers of antibody (>1 to 12,800) as shown in FIG. 1D. This hybridoma was subsequently cloned, expanded, and purified. Purified antibody KK1.23 is specific for human IL-15Rα as shown by Western blot analysis in FIG. 1E. In addition, KK1.23 appears to bind to human IL-15Rα with a higher affinity than the commercially available antibody (FIG. 1E).

pIL-15Rα Expresses Bioactive Protein

Figure 2A:
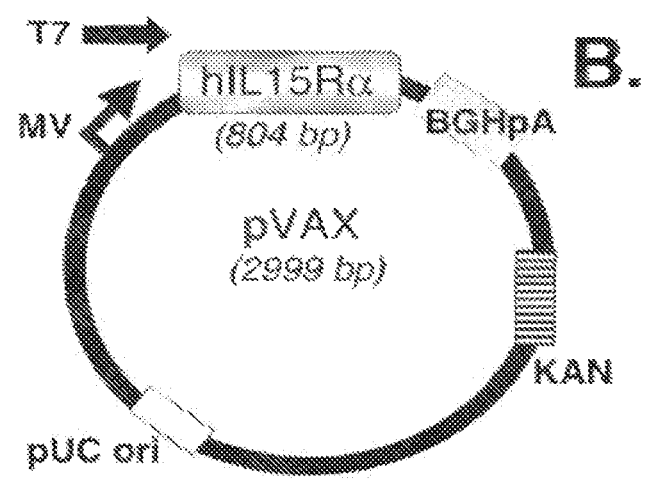
FIGS. 2A-2G relates to the construction and expression of the IL-15Rα DNA plasmid.
Figure 2B:
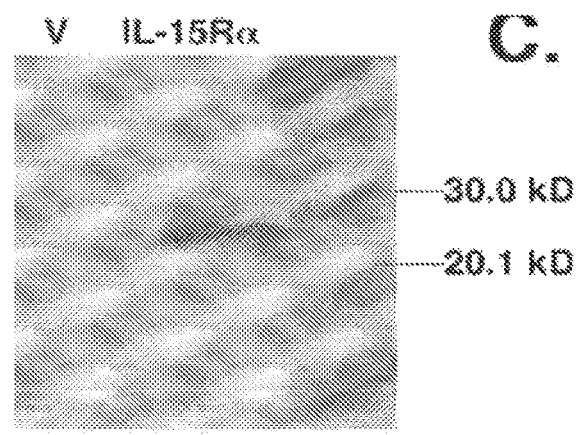
Figure 2C:
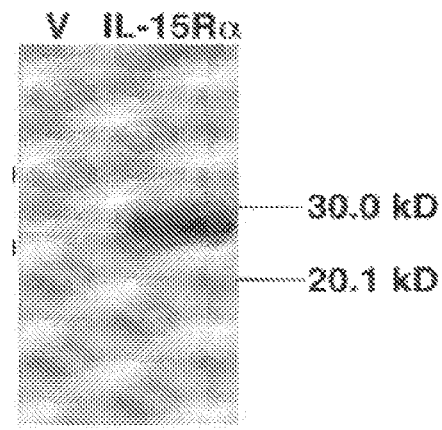

An IL-15Rα expression vector was created that was suitable for use in vaccination studies. The human IL-15Rα ORF was cloned into the pVAX1 expression vector as shown in FIG. 2A, under the control of the CMV promoter. To assess the appropriate expression of the IL-15Rα plasmid, an in vitro translation assay was carried out. The S35 radiolabeled protein is shown in FIGS. 2B & 2C migrating at roughly 30.0 kD, whereas the control plasmid, pVAX, did not yield any detectable protein product as expected. The commercial R&D (2B) or the KK1.23 (2C) antibody against human IL-15Rα was utilized to immunoprecipitate the radiolabeled protein.

Figure 2D:
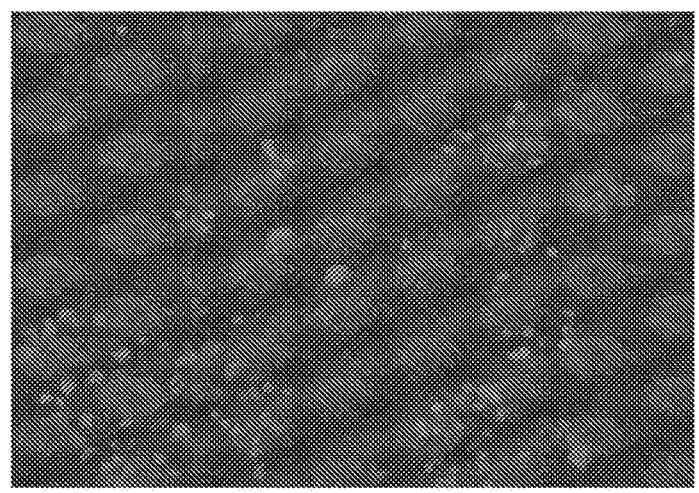
Figure 2E:
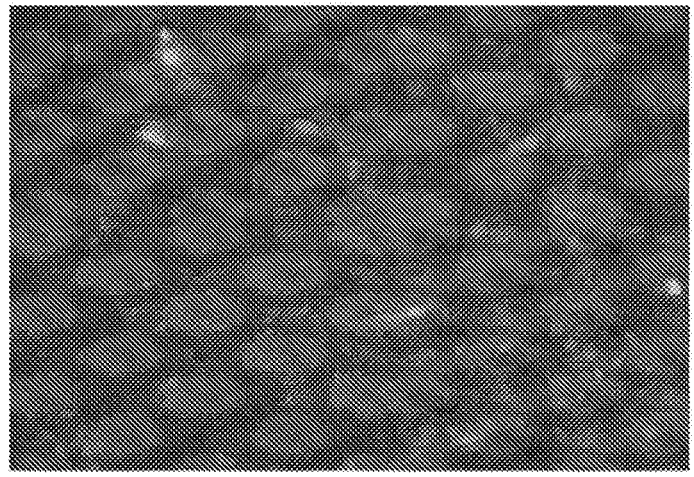
Figure 2F:
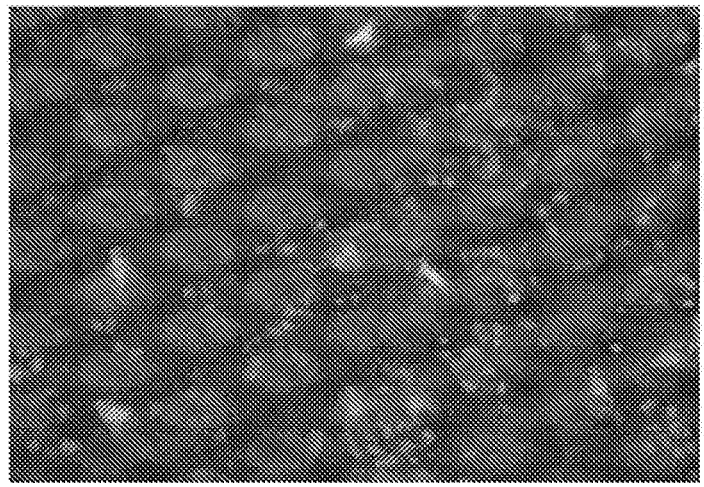
Figure 2G:
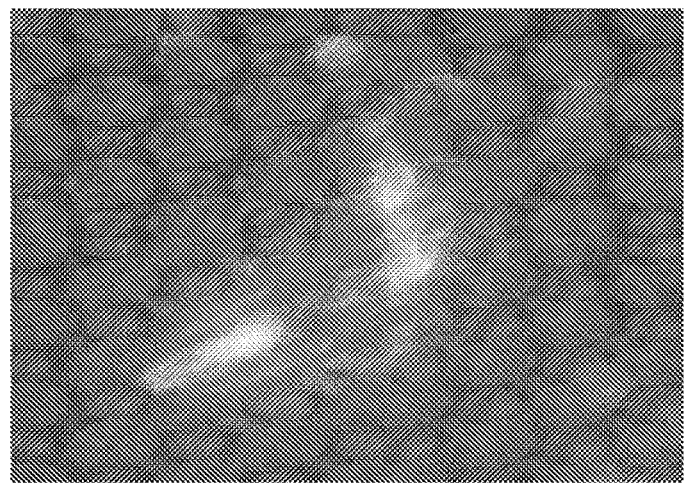

To confirm expression of the plasmid IL-15Rα, an immunoflourescence assay was performed using the KK1.23 antibody from Example I, above. The ORF of human IL-15Rα was cloned into the pTRACER expression vector, which also encodes for the green fluorescent protein (GFP) reporter. Therefore, cells fluorescing green (FIG. 2E-G) also express pIL-15Rα. The KK1.23 anti-human IL-15Rα is detected using anti-mouse IgG-PE (Red). The untransfected control is shown in FIG. 2D, and the isotype control in FIG. 2E. The data illustrates both the ability of the pIL-15Rα plasmid to express as well as the ability of the anti-human pIL-15Rα antibody to detect the translated protein product. The pIL-15Rα plasmid encodes for a conformationally accurate and surface localized protein.

Combining pIL-15 and pIL-15Rα as an Adjuvant

Figure 3A:
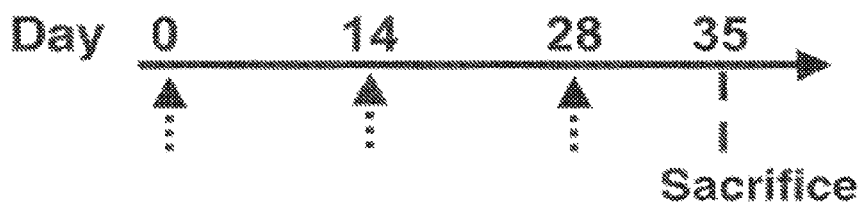
FIGS. 3A-3C show that the combination of pIL-15 and pIL-15Rα augments immune responses compared to either plasmid delivered alone.
Figure 3B:
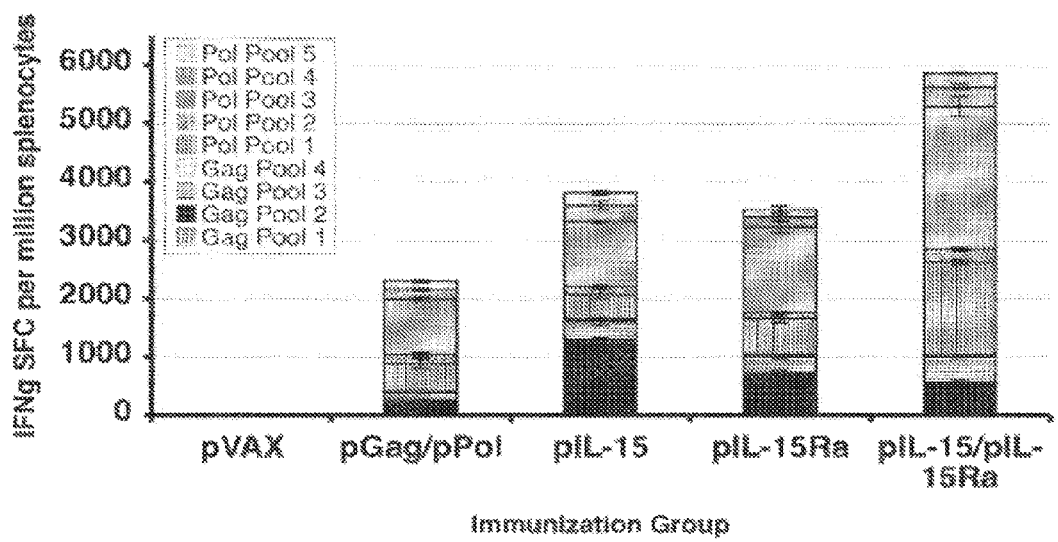
Figure 3C:
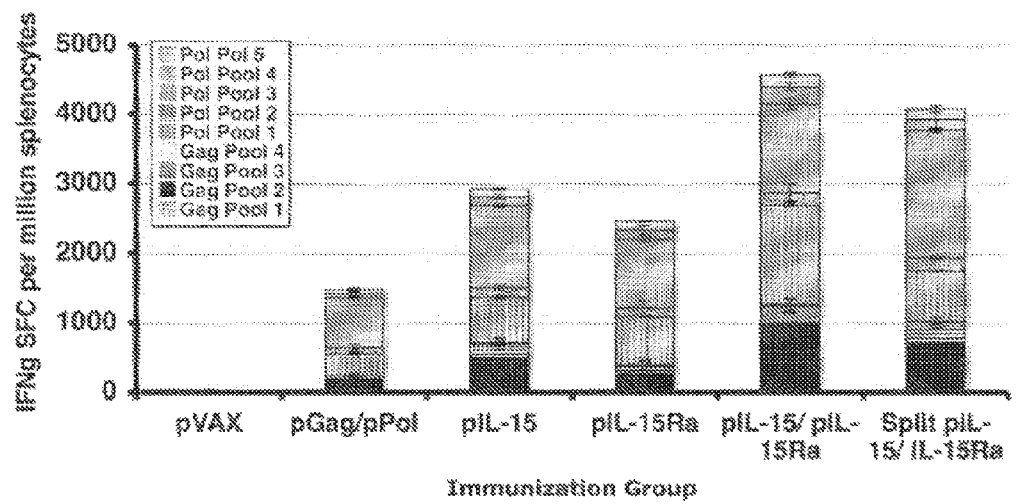

To examine the ability of pIL-15Rα to enhance immune responses as compared with pIL-15, BALB/c mice were immunized intramuscularly in the tibialis anterior muscle accompanied by in vivo electorporation, according to the schedule shown in FIG. 3A. Mice were immunized with either pVAX control vector, or 5 µg of antigenic constructs (HIV-1 gag, HIV-1 pol) with 10 µg of pIL-15, 15 µg of pIL-15Rα, or both pIL-15 and pIL-15Rα in a final volume of 40 ul. These doses were predetermined to give optimal responses in preliminary studies (data not shown). As shown in FIG. 3B, immunization with antigenic constructs alone resulted in 2,300 spot forming cells (SFC)/106 splenocytes as measured by IFN-γ ELISpot. The addition of pIL-15 enhanced the response to 3,800 SFC, while co-immunization with pIL-15Rα and pIL-15 exhibited the most dramatic increase over the antigenic group alone, resulting in 5,900 SFC. These results support the idea that the formation of the IL-15/IL-15Rα immune complex can serve as a more potent adjuvant than IL-15 alone.

Figure 4A:
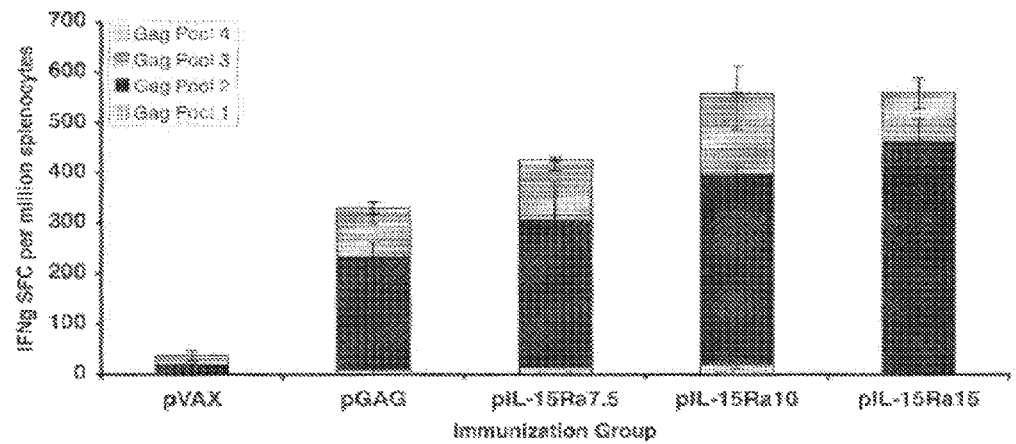
FIGS. 4A and 4B show that IL-15Rα DNA plasmid is immunogenic in a dose-dependent manner without pIL-15. BALB/c mice were immunized as shown in FIG. 3A with DNA formulations containing combinations of vector, 5 µg of antigenic plasmid (HIV-1 gag and pol), and increasing does of IL-15Rα (7.5, 10, or 15 µg). IFN-γ ELIspot was carried out on splenocytes stimulated with R10 (negative control), ConA (positive control), and HIV-1 gag peptide pools or HIV-1 pol peptide pools. Data from experiments using HIV-1 gag peptide pools are shown in FIG. 4A. Data from experiments using HIV-1 pol peptide pools are shown in FIG. 4B.
Figure 4B:
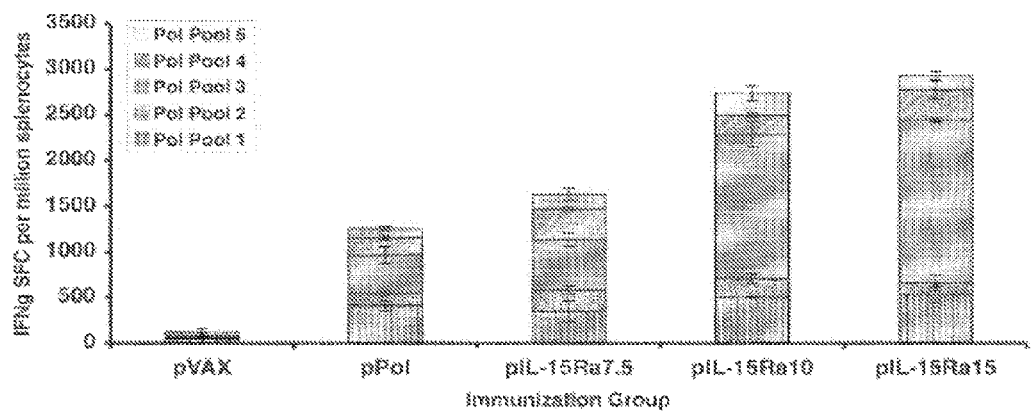

To determine whether this immune complex was truly being formed in vivo, another immunization group was added in which the pIL-15 and pIL-15Rα were injected (with antigen) in separate legs. In this split delivery method, plasmid-delivered IL-15 and IL-15Rα would be unable to form an immune complex. The co-immunization of pIL-15 and IL-15Rα in separate legs was found to elicit levels of IFN-γ similar to those observed with the same combination delivered in the same leg (4,562 vs. 4,072 SFC, respectively). It is noted that the immunization group with antigenic construct and pIL-15Rα also augmented antigen specific IFN-γ secretion to approximately 3500 SFC (FIG. 3B). To confirm these results, we immunized a new set of mice with increasing doses of pIL-15Rα plasmid in conjunction with antigenic constructs to see if the pIL-15Rα would induce responses in a dose-dependent fashion. As shown in FIG. 4, the inclusion of pIL-15Rα did enhance the induced IFN-γ secretion in a dose dependent fashion, in measured responses against pGag (Panel A) or pPol (Panel B). Regardless of the HIV-1 antigenic construct used, co-immunization with pIL-15Rα augmented cellular immune responses by 1.5 to 2 fold at the highest dose used. Notably, IL-15Rα appears to enhance antigen specific immune responses even in the absence of IL-15.

Figure 5A:
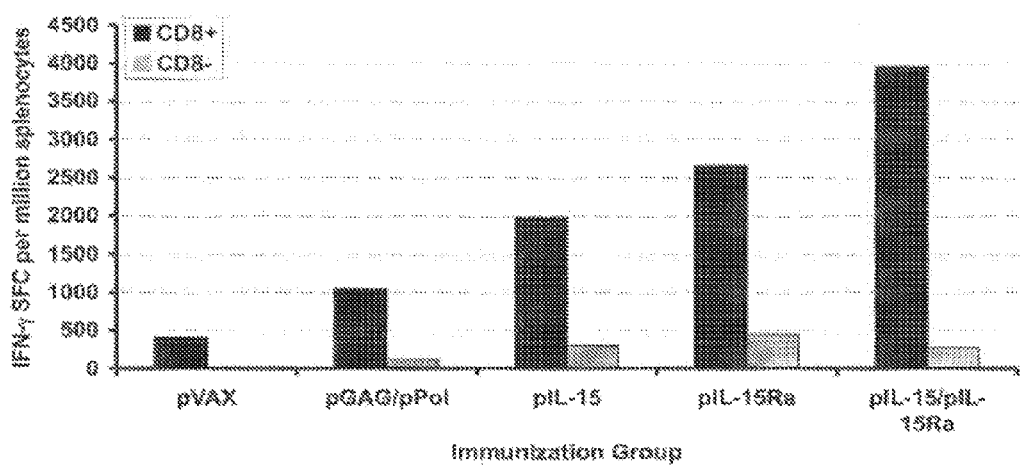
FIGS. 5A and 5B show that pIL-15Rα augments IFN-γ secretion primarily by CD8+ T cells. The contribution of IFN-γ secretion by CD8+ T cells was measured by ex vivo depletion of CD8+ T cells from the splenocytes of immunized mice using Miltenyi beads.

To further confirm the adjuvant properties of pIL-15Rα, the effector functions of CD4+ and CD8+ T cells after vaccination were examined. CD8+ T cells were depleted from splenocytes of mice immunized with each vaccine combination previously mentioned, above, prior to carrying out the IFN-γ ELISpot assay. As shown in FIG. 5A, the depletion of CD8+ T cells from the splenocytes of mice immunized with either pIL-15, pIL-15Rα or the combination of both significantly decreased the amount of IFN-γ secretion detected. There was no difference between the CD4+ T cell contribution (grey bars) in any of the immunized groups, compared to the total responses observed in whole splenocytes (black bars). Taken together, the combination of pIL-15Rα and pIL-15 in a vaccination strategy greatly enhance the immune response over either construct delivered alone. This additive effect primarily acts on CD8+T cells, as the effect was lost with the depletion of this cell population.

Figure 5B:
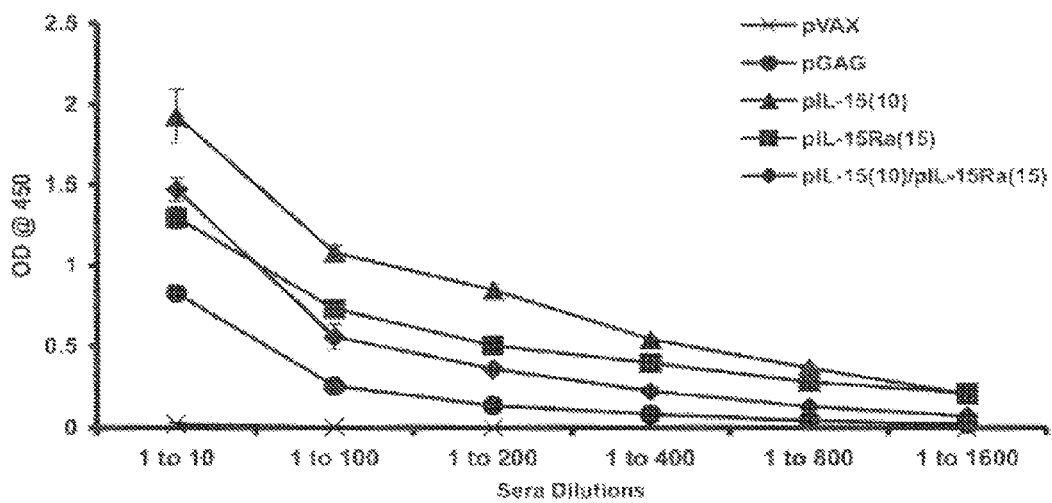

To determine whether pIL-15Rα would also have an effect on humoral immune responses, antibody responses elicited through each vaccination strategy were also measured by ELISA. Sera from immunized mice was assayed to measure the levels of IgG antibodies against the HIV-1 Gag (p24) protein (FIG. 5B). While the combination of pIL-15 and pIL-15Rα was the best at eliciting cellular immunity, mice immunized with either pIL-15 or pIL-15Rα alone had the highest titers of HIV-1 specific antibodies (1:1600) compared to mice immunized with pVAX (not detected), pGag alone or the combination (1:800).

The pIL-15Rα Adjuvant does not Appear to Enhance CD8+ T Cell Memory

Figure 6A:
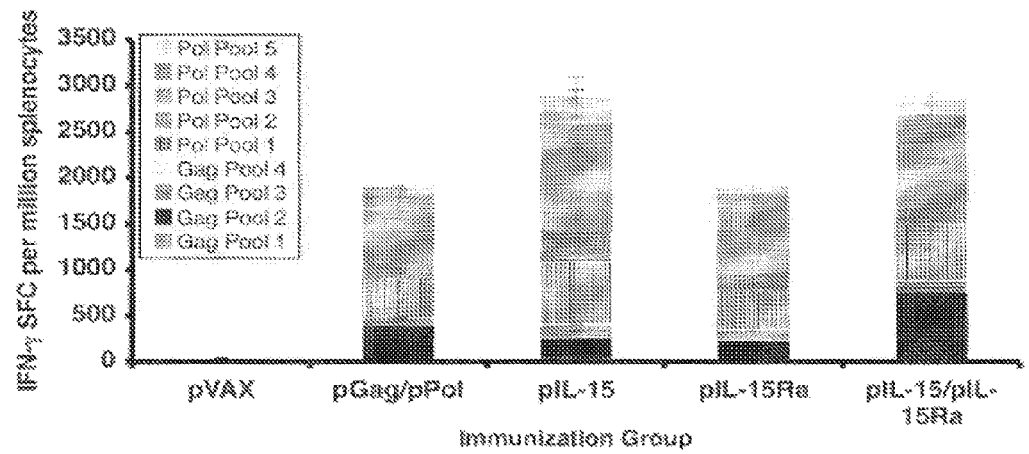
FIGS. 6A to 6C shows that the combination of pIL-15 and pIL-15Rα does not enhance memory responses. Mice were immunized three times and rested for 30 weeks before sacrificing.
Figure 6B:
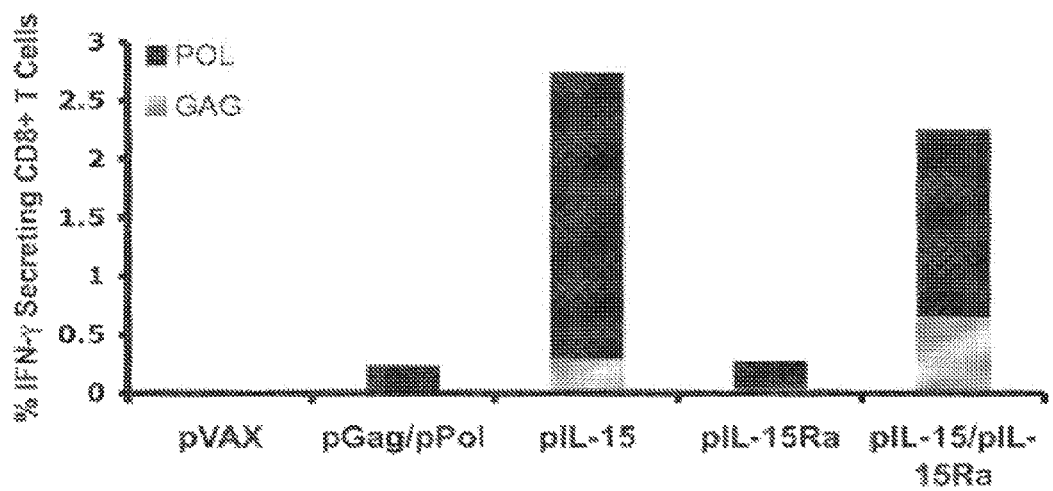

Mice were immunized three times as previously mentioned, herein; however, instead of sacrificing these animals one week post the third immunization, they were allowed to rest for approximately 30 weeks to be sure the responses observed would be contributed primarily by the memory population. As shown in FIG. 6A, the responses after a significant rest period were still quite robust. The mice immunized with the antigenic construct alone had responses around 1700 SFC. The highest responses were clearly in groups of mice co-immunized with pIL-15, ~2800 SFC for both pIL-15 and pIL-15/pIL-15Ra combination. In mice co-immunized with pIL-15Rα in the absence of pIL-15, an adjuvant affect was no longer observed (~1700 SFC). The same trends were also observed by intracellular cytokine staining and flow cytometry (FIG. 6B) where the level of IFN-γ production by CD8+ T cells was most pronounced in mice coimmunized with pIL-15. The addition of pIL-15Rα in the vaccination strategy was observed to have little effect on memory responses, whereas pIL-15 was observed to have a large effect. Thus, supporting the theory that while pIL-15Rα was a robust adjuvant early after vaccination, over time IL-15 appears to be a better inducer of memory CD8+ T cells.

Figure 6C:
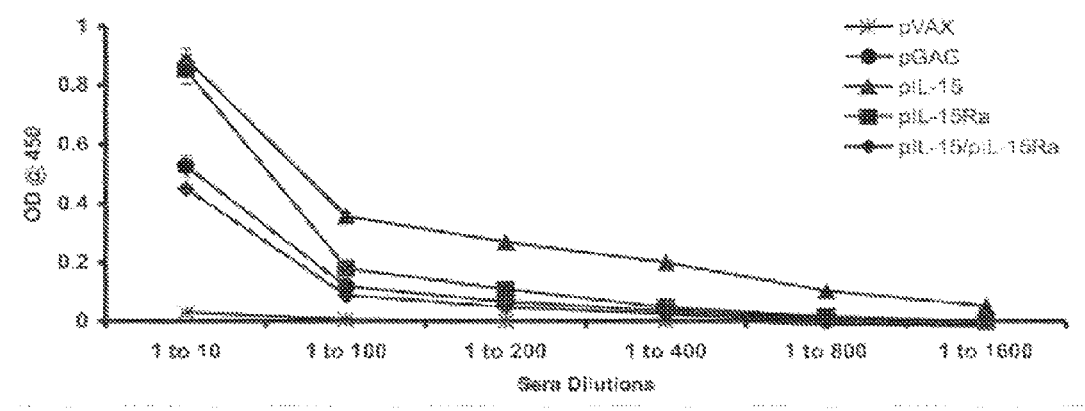

The memory antibody response was similar to that observed during the effector phase. As shown in FIG. 6C, mice immunized with pIL-15 had detectable antibodies against HIV-1 Gag (p24) at dilutions out to 1:1600, whereas all other groups, including the combination of pIL-15/pIL-15Rα, diluted out at 1:400. While pIL-15 shows to be an effective adjuvant in the generation of humoral as well as cellular memory responses; pIL-15Rα, on the on the other hand, appears to play role in accelerating the acute immune response to antigen.

pIL-15Rα Adjuvant without IL-15

Figure 7A:
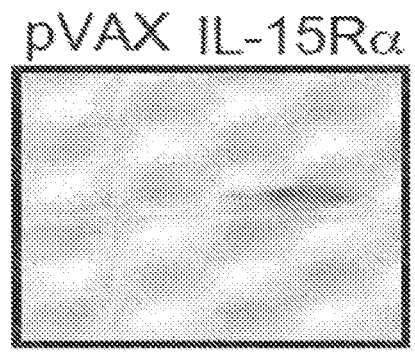
FIGS. 7A to 7C show that pIL-15Rα can adjuvant in the absence of endogenous IL-15. To explore the mechanism of IL-15Rα as an adjuvant, we looked at the ability of human IL-15Rα to bind murine IL-15.
Figure 7A:
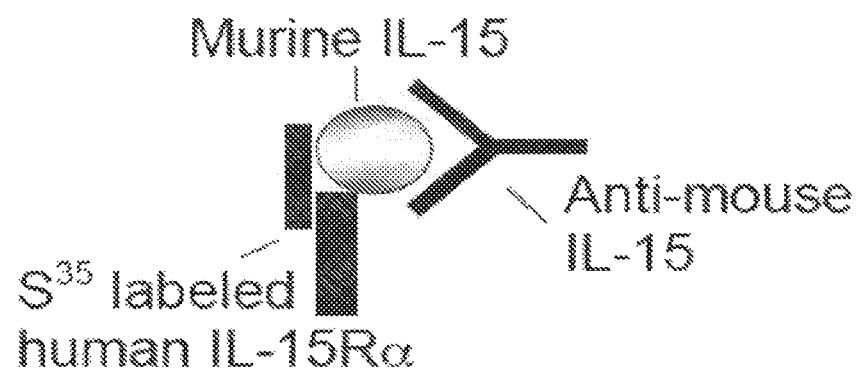

To test whether human IL-15Rα protein could be augmenting immune responses in vaccinated mice by forming complexes with endogenous murine IL-15, or independently of IL-15, vaccinations were studied in IL-15 knockout mice. Initially, as a control, translated human IL-15Rα protein was tested for binding to mouse IL-15. As shown in FIG. 7A, S35 radiolabeled human IL-15Rα protein incubated with murine IL-15 was able to be immunoprecipitated with an anti-mouse IL-15 antibody suggesting the ability of murine IL-15 to bind to human IL-15Rα.

Figure 7B:
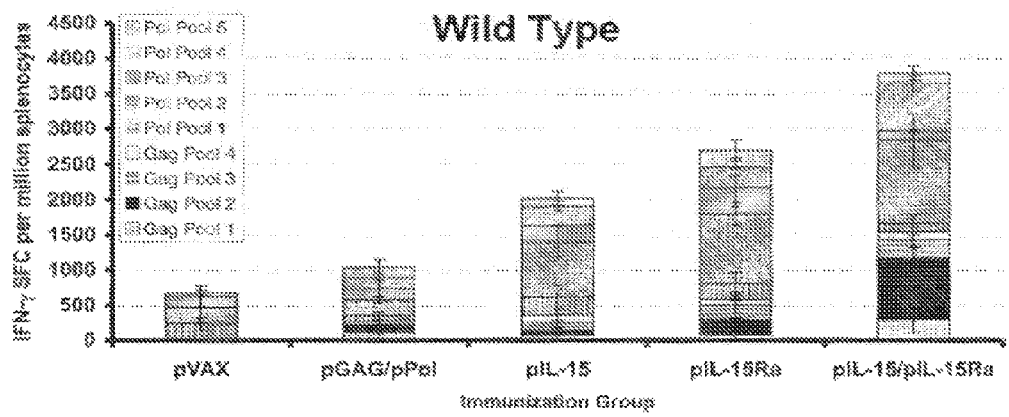
Figure 7C:
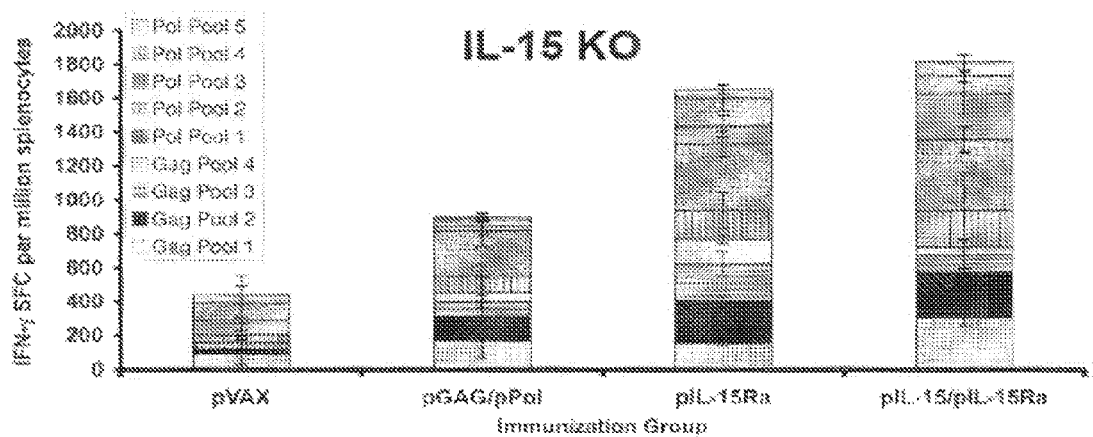

The ability of pIL-15Rα to adjuvant in the absence of murine IL-15 was examined. Accordingly, the same vaccination studies in IL-15 knockout mice were conducted, which lack endogenous IL-15 and as a result have a deficiency in NK and memory CD8+ T cells (Kennedy et al., 2000). FIG. 7C shows that pIL-15Rα adjuvants the immune responses in the absence of endogenous murine IL-15 in the knockout mice, as determined by IFN-γ ELISpot. Furthermore, the combination of pIL-15 and pIL-15Rα fails to further enhance the immune response by either adjuvant administered alone as initially observed in BALB/c mice. The IL-15-/- mice were generated on a C57/BL6 background from Taconic. Therefore, to verify we would get similar responses in the appropriate background control mice as were observed in BALB/c, the same experiments were repeated. FIG. 7B shows the results from the control mice immunized with the identical schedule and shows the same trend as BALB/c immunized mice.

CONCLUSION

Coimmunization of the IL-15Rα construct together with a human IL-15 and HIV-1 antigenic DNA constructs resulted in levels of IFN-γ secretion that were 2.5 fold more potent than immunization with the antigenic constructs alone (FIG. 3B). The IFN-γ secretion was attributable to CD8+ T cells as the depletion of these cells prior to plating on the ELISpot resulted in 10 fold less IFN-γ secretion. The increased potency observed with the combined delivery of IL-15/IL-15Rα is not likely due to the formation of a stable complex in transfected cells as injecting these pIL-15 and pIL-15Ra into separate legs (with antigen) also elicited immune responses similar to delivery in the same leg. It is therefore more likely that the enhanced response observed with the co-delivery of pIL-15/pIL-15Rα is an additive effect of two independent adjuvants. Co-delivery of these two adjuvants did not appear to further enhance humoral immune responses as measured by IgG antibodies in the sera.

The long-term effects of the combined pIL-15/pIL-15Rα on the immune response was also examined. In order to observe the memory responses, 30 weeks after the third immunization was allowed to pass prior to carrying out immune analysis. The results showed that although the combination of these two adjuvants elicits potent CD8+ T cell responses in the early phase of an immune response, the effect on memory T cells is primarily observed only in mice immunized along with pIL-15. The inclusion of pIL-15 was needed for an enhanced memory immune response over the antigen alone. Similarly, IL-15Rα initially elicited immune responses equal to or greater than that IL-15, but it did not help to sustain the memory response. Therefore, while IL-15Rα expanded burst size, burst size in the absence of the IL-15 signal for memory was not enough to sustain a long-term response.

In a surprising observation, the delivery of the antigenic plasmid with pIL-15Rα also augmented cellular immune responses, and equal to those elicited by pIL-15. To be certain, immunizations were performed with increasing amounts of pIL-15Rα and dose-dependent responses were observed. It may be that the human IL-15Rα protein was able to bind to endogenous murine IL-15 and transpresent it in a similar fashion since murine IL-15 is ~73% identical to the human IL-15 (Anderson et al., 1995a). To test this hypothesis, IL-15 knockout mice, which lack any endogenous IL-15, were immunized. An approximate 2 fold increase in the IL-15 knockout mice immunized with pIL-15Rα over antigen alone was observed. Due to the difficulty of obtaining IL-15-/- female mice in large numbers between the ages of 6-8 weeks, the pIL-15 group from these experiments were excluded. However, the enhanced effect of the combination of pIL-15/pIL-15Rα was no longer observed. It should be noted that control C57/BL6 mice exhibited the same trends that were seen in BALB/c mice (albeit lower total spot counts and higher background in the pVAX group) and that the IL-15 knockout mice had overall lower responses even compared to the C57/BL6 mice. These mice have been previously described to have somewhat defective host defense responses including the inability to protect against a vaccinia challenge (Kennedy et al., 2000). Regardless of the overall lower immune responses, the adjuvanting effect of pIL-15Rα was still observed in the absence of any endogenous IL-15. While not intending to be bound by this theory, considering the full complement of results, it is believed that IL-15Rα can serve as a novel adjuvant capable of eliciting responses independently of IL-15. This amplification of the immune response appears particularly focused on immune expansion during the acute phase rather than the memory phase of the host T cell response.

REFERENCES

AMARA, R. R., VILLINGER, F., ALTMAN, J. D., LYDY, S. L., O'NEIL, S. P., STAPRANS, S. I., MONTEFIORI, D. C., XU, Y., HERNDON, J. G., WYATT, L. S., CANDIDO, M. A., KOZYR, N. L., EARL, P. L., SMITH, J. M., MA, H. L., GRIMM, B. D., HULSEY, M. L., MILLER, J., MCCLURE, H. M., MCNICHOLL, J. M., MOSS, B., and ROBINSON, H. L. (2001). Control of a mucosal challenge and prevention of AIDS by a multiprotein DNA/MVA vaccine. Science (New York, N.Y. 292, 69-74.

ANDERSON, D. M., JOHNSON, L., GLACCUM, M. B., COPELAND, N. G., GILBERT, D. J., JENKINS, N. A., VALENTINE, V., KIRSTEIN, M. N., SHAPIRO, D. N., MORRIS, S. W., and ET AL. (1995a). Chromosomal assignment and genomic structure of Il15. Genomics 25, 701-706.

ANDERSON, D. M., KUMAKI, S., AHDIEH, M., BERTLES, J., TOMETSKO, M., LOOMIS, A., GIRI, J., COPELAND, N. G., GILBERT, D. J., JENKINS, N. A., and ET AL. (1995b). Functional characterization of the human interleukin-15 receptor alpha chain and close linkage of IL15RA and IL2RA genes. The Journal of biological chemistry 270, 29862-29869.

BAMFORD, R. N., DEFILIPPIS, A. P., AZIMI, N., KURYS, G., and WALDMANN, T. A. (1998). The untranslated region, signal peptide, and the coding sequence of the carboxyl terminus of IL-15 participate in its multifaceted translational control. J Immunol 160, 4418-4426.

BAROUCH, D. H., SANTRA, S., SCHMITZ, J. E., KURODA, M. J., FU, T. M., WAGNER, W., BILSKA, M., CRAIU, A., ZHENG, X. X., KRIVULKA, G. R., BEAUDRY, K., LIFTON, M. A., NICKERSON, C. E., TRIGONA, W. L., PUNT, K., FREED, D. C., GUAN, L., DUBEY, S., CASIMIRO, D., SIMON, A., DA VIES, M. E., CHASTAIN, M., STROM, T. B., GELMAN, R. S., MONTEFIORI, D. C., LEWIS, M. G., EMINI, E. A., SHIVER, J. W., and LETVIN, N. L. (2000). Control of viremia and prevention of clinical AIDS in rhesus monkeys by cytokine-augmented DNA vaccination. Science (New York, N.Y. 290, 486-492.

BECKER, T. C., WHERRY, E. J., BOONE, D., MURALI-KRISHNA, K., ANTIA, R., MA, A., and AHMED, R. (2002). Interleukin 15 is required for proliferative renewal of virus-specific memory CD8 T cells. The Journal of experimental medicine 195, 1541-1548.

BERGAMASCHI, C, ROSATI, M., JALAH, R., VALENTIN, A., KULKARNI, V., ALICEA, C, ZHANG, G. M., PATEL, V., FELBER, B. K., and PAVLAKIS, G. N. (2008). Intracellular interaction of interleukin-15 with its receptor alpha during production leads to mutual stabilization and increased bioactivity. The Journal of biological chemistry 283, 4189-4199.

BETTS, M. R., KROWKA, J. F., KEPLER, T. B., DAVIDIAN, M., CHRISTOPHERSON, C, KWOK, S., LOUIE, L., ERON, J., SHEPPARD, H., and FRELINGER, J. A. (1999). Human immunodeficiency virus type 1-specific cytotoxic T lymphocyte activity is inversely correlated with HIV type 1 viral load in HIV type 1-infected long-term survivors. AIDS research and human retroviruses 15, 1219-1228.

BOYER, J. D., ROBINSON, T. M., KUTZLER, M. A., VANSANT, G, HOKEY, D. A., KUMAR, S., PARKINSON, R., WU, L., SIDHU, M. K., PAVLAKIS, G. N., FELBER, B. K., BROWN, C, SILVERA, P., LEWIS, M. G., MONFORTE, J., WALDMANN, T. A., ELDRIDGE, J., and WEINER, D. B. (2007). Protection against simian/human immunodeficiency virus (SHIV) 89.6P in macaques after coimmunization with SHIV antigen and IL-15 plasmid. Proceedings of the National Academy of Sciences of the United States of America 104, 18648-18653.

BULANOVA, E., BUDAGIAN, V., POHL, T., KRAUSE, H., DURKOP, H., PAUS, R., and BULFONE-PAUS, S. (2001). The IL-15R alpha chain signals through association with Syk in human B cells. J Immunol 167, 6292-6302.

BURKETT, P. R., KOKA, R., CHIEN, M., CHAI, S., BOONE, D. L., and MA, A. (2004). Coordinate expression and trans presentation of interleukin (IL)-15Ralpha and IL-15 supports natural killer cell and memory CD8+ T cell homeostasis. The Journal of experimental medicine 200, 825-834.

BURKETT, P. R., KOKA, R., CHIEN, M., CHAI, S., CHAN, F., MA, A., and BOONE, D. L. (2003). IL-15R alpha expression on CD8+ T cells is dispensable for T cell memory. Proceedings of the National Academy of Sciences of the United States of America 100, 4724-4729.

CALAROTA, S. A., DAI, A., TROCIO, J. N., WEINER, D. B., LORI, F., and LISZIEWICZ, J. (2008). IL-15 as memory T-cell adjuvant for topical HIV-1 DermaVir vaccine. Vaccine.

CAO, Y., QIN, L., ZHANG, L., SAFRIT, J., and HO, D. D. (1995). Virologic and immunologic characterization of long-term survivors of human immunodeficiency virus type 1 infection. The New England journal of medicine 332, 201-208.

DUBOIS, S., MARINER, J., WALDMANN, T. A., and TAGAYA, Y. (2002). IL-15Ralpha recycles and presents IL-15 In trans to neighboring cells. Immunity 17, 537-547.

DUITMAN, E. H., ORINSKA, Z., BULANOVA, E., PAUS, R., and BULFONE-PAUS, S. (2008). How a cytokine is chaperoned through the secretory pathway by complexing with its own receptor: lessons from IL-15/IL-15R{alpha}. Molecular and cellular biology.

FULLER, D. H., LOUDON, P., and SCHMALJOHN, C. (2006). Preclinical and clinical progress of particle-mediated DNA vaccines for infectious diseases. Methods (San Diego, Calif. 40, 86-97.

GAO, F., LI, Y., DECKER, J. M., PEYERL, F. W., BIBOLLET-RUCHE, F., RODENBURG, CM., CHEN, Y., SHAW, D. R., ALLEN, S., MUSONDA, R., SHAW, G. M., ZAJAC, A. J., LETVIN, N., and HAHN, B. H. (2003). Codon usage optimization of HIV type 1 subtype C gag, pol, env, and nef genes: in vitro expression and immune responses in DNA-vaccinated mice. AIDS research and human retroviruses 19, 817-823.

GIRI, J. G., AHDIEH, M. EISENMAN, J., SHANEBECK, K., GRABSTEIN, K. KUMAKI, S., NAMEN, A., PARK, L. S., COSMAN, D., and ANDERSON, D. (1994). Utilization of the beta and gamma chains of the IL-2 receptor by the novel cytokine IL-15. The EMBO journal 13, 2822-2830.

GIRI, J. G., ANDERSON, D. M., KUMAKI, S. PARK, L. S., GRABSTEIN, K. H., and COSMAN, D. (1995). IL-15, a novel T cell growth factor that shares activities and receptor components with IL-2. Journal of leukocyte biology 57, 763-766.

HALWANI, R., BOYER, J. D., YASSINE-DIAB, B., HADDAD, E. K., ROBINSON, T. M., KUMAR, S., PARKINSON, R., WU, L., SIDHU, M. K., PHILLIPSON-WEINER, R., PAVLAKIS, G. N., FELBER, B. K., LEWIS, M. G., SHEN, A., SILICIANO, R. F., WEINER, D. B., and SEKALY, R. P. (2008). Therapeutic vaccination with simian immunodeficiency virus (SIV)-DNA+IL-12 or IL-15 induces distinct CD8 memory subsets in SIV-infected macaques. J Immunol 180, 7969-7979.

HOKEY, D. A., and WEINER, D. B. (2006). DNA vaccines for HIV: challenges and opportunities. Springer seminars in immunopathology 28, 267-279.

JIN, X., BAUER, D. E., TUTTLETON, S. E., LEWIN, S., GETTIE, A., BLANCHARD, J., IRWIN, C. E., SAFRIT, J. T., MITTLER, J., WEINBERGER, L., KOSTRIKIS, L. G., ZHANG, L., PERELSON, A. S., and HO, D. D. (1999). Dramatic rise in plasma viremia after CD8(+) T cell depletion in simian immunodeficiency virus-infected macaques. The Journal of experimental medicine 189, 991-998.

KENNEDY, M. K., GLACCUM, M., BROWN, S. N., BUTZ, E. A., VINEY, J. L., EMBERS, M., MATSUKI, N., CHARRIER, K., SEDGER, L., WILLIS, C. R., BRASEL, K., MORRISSEY, P. J., STOCKING, K., SCHUH, J. C., JOYCE, S., and PESCHON, J. J. (2000). Reversible defects in natural killer and memory CD8 T cell lineages in interleukin 15-deficient mice. The Journal of experimental medicine 191, 771-780.

KHAN, A. S., SMITH, L. C., ABRUZZESE, R. V., CUMMINGS, K. K., POPE, M. A., BROWN, P. A., and DRAGHIA-AKLI, R. (2003). Optimization of electroporation parameters for the intramuscular delivery of plasmids in pigs. DNA and cell biology 22, 807-814.

KIM, J. J., NOTTINGHAM, L. K., SIN, J. I., TSAI, A., MORRISON, L., OH, J., DANG, K., HU, Y., KAZAHAYA, K., BENNETT, M., DENTCHEV, T., WILSON, D. M., CHALIAN, A. A., BOYER, J. D., AGADJANYAN, M. G., and WEINER, D. B. (1998). CD8 positive T cells influence antigen-specific immune responses through the expression of chemokines. The Journal of clinical investigation 102, 1112-1124.

KOKA, R., BURKETT, P., CHIEN, M., CHAI, S., BOONE, D. L., and MA, A. (2004). Cutting edge: murine dendritic cells require IL-15R alpha to prime NK cells. J Immunol 173, 3594-3598.

KOUP, R. A., SAFRIT, J. T., CAO, Y., ANDREWS, C. A., MCLEOD, G. BORKOWSKY, W., FARTHING, C, and HO, D. D. (1994). Temporal association of cellular immune responses with the initial control of viremia in primary human immunodeficiency virus type 1 syndrome. Journal of virology 68, 4650-4655.

KU, C. C., MURAKAMI, M., SAKAMOTO, A., KAPPLER, J., and MARRACK, P. (2000). Control of homeostasis of CD8+ memory T cells by opposing cytokines. Science (New York, N.Y. 288, 675-678.

KUTZLER, M. A., ROBINSON, T. M., CHATTERGOON, M. A., CHOO, D. K., CHOO, A. Y., CHOE, P. Y., RAMANATHAN, M. P., PARKINSON, R., KUDCHODKAR, S., TAMURA, Y., SIDHU, M., ROOPCHAND, V., KIM, J. J., PAVLAKIS, G. N., FELBER, B. K., WALDMANN, T. A., BOYER, J. D., and WEINER, D. B. (2005). Coimmunization with an optimized IL-15 plasmid results in enhanced function and longevity of CD8 T cells that are partially independent of CD4 T cell help. J Immunol 175, 112-123.

LADDY, D. J., YAN, J., KUTZLER, M., KOBASA, D., KOBINGER, G. P., KHAN, A. S., GREENHOUSE, J., SARDESAI, N. Y., DRAGHIA-AKLI, R., and WEINER, D. B. (2008). Heterosubtypic protection against pathogenic human and avian influenza viruses via in vivo electroporation of synthetic consensus DNA antigens. PLoS ONE 3, e2517.

LEIFERT, J. A., RODRIGUEZ-CARRENO, M. P., RODRIGUEZ, F., and WHITTON, J. L. (2004). Targeting plasmid-encoded proteins to the antigen presentation pathways. Immunological reviews 199, 40-53.

LI, W., LI, S., HU, Y., TANG, B., CUI, L., and HE, W. (2008). Efficient augmentation of a long-lasting immune responses in HIV-1 gag DNA vaccination by IL-15 plasmid boosting. Vaccine 26, 3282-3290.

LODOLCE, J. P., BOONE, D. L., CHAI, S., SWAIN, R. E., DASSOPOULOS, T., TRETTIN, S., and MA, A. (1998). IL-15 receptor maintains lymphoid homeostasis by supporting lymphocyte homing and proliferation. Immunity 9, 669-676.

LODOLCE, J. P., BURKETT, P. R., BOONE, D. L., CHIEN, M., and MA, A. (2001). T cell-independent interleukin 15Ralpha signals are required for bystander proliferation. The Journal of experimental medicine 194, 1187-1194.

LUCAS, M., SCHACHTERLE, W., OBERLE, K. AICHELE, P., and DIEFENBACH, A. (2007). Dendritic cells prime natural killer cells by trans-presenting interleukin 15. Immunity 26, 503-517.

MESTECKY, J., JACKSON, S., MOLDOVEANU, Z., NESBIT, L. R., KULHAVY, R., PRINCE, S. J., SABBAJ, S., MULLIGAN, M. J., and GOEPFERT, P. A. (2004). Paucity of antigen-specific IgA responses in sera and external secretions of HIV-type 1-infected individuals. AIDS Res Hum Retroviruses 20, 972-988.

MOORE, A. C., KONG, W. P., CHAKRABARTI, B. K., and NABEL, G. J. (2002). Effects of antigen and genetic adjuvants on immune responses to human immunodeficiency virus DNA vaccines in mice. Journal of virology 76, 243-250.

MORROW, M. P., and WEINER, D. B. (2008). Cytokines as adjuvants for improving anti-HIV responses. AIDS (London, England) 22, 333-338.

MUSEY, L., HUGHES, J., SCHACKER, T., SHEA, T., COREY, L., and MCELRATH, M. J. (1997). Cytotoxic-T-cell responses, viral load, and disease progression in early human immunodeficiency virus type 1 infection. The New England journal of medicine 337, 1267-1274.

OGAWA, T., TARKOWSKI, A., MCGHEE, M. L., MOLDOVEANU, Z., MESTECKY, J., HIRSCH, H. Z., KOOPMAN, W. J., HAMADA, S., MCGHEE, J. R., and KIYONO, H. (1989). Analysis of human IgG and IgA subclass antibody-secreting cells from localized chronic inflammatory tissue. J Immunol 142, 1150-1158.

OGG, G. S., JIN, X., BONHOEFFER, S., DUNBAR, P. R., NOWAK, M. A., MONARD, S., SEGAL, J. P., CAO, Y., ROWLAND-JONES, S. L., CERUNDOLO, V., HURLEY, A., MARKOWITZ, M., HO, D. D., NIXON, D. F., and MCMICHAEL, A. J. (1998). Quantitation of HIV-1-specific cytotoxic T lymphocytes and plasma load of viral RNA. Science (New York, N.Y. 279, 2103-2106.

OH, S., BERZOFSKY, J. A., BURKE, D. S., WALDMANN, T. A., and PERERA, L. P. (2003). Coadministration of HIV vaccine vectors with vaccinia viruses expressing IL-15 but not IL-2 induces long-lasting cellular immunity. Proceedings of the National Academy of Sciences of the United States of America 100, 3392-3397.

OH, S., PERERA, L. P., BURKE, D. S., WALDMANN, T. A., and BERZOFSKY, J. A. (2004). IL-15/IL-15Ralpha-mediated avidity maturation of memory CD8+ T cells. Proceedings of the National Academy of Sciences of the United States of America 101, 15154-15159.

OH, S., PERERA, L. P., TERABE, M., NI, L., WALDMANN, T. A., and BERZOFSKY, J. A. (2008). IL-15 as a mediator of CD4+ help for CD8+ T cell longevity and avoidance of TRAIL-mediated apoptosis. Proceedings of the National Academy of Sciences of the United States of America 105, 5201-5206.

ONU, A., POHL, T., KRAUSE, H., and BULFONE-PAUS, S. (1997). Regulation of IL-15 secretion via the leader peptide of two IL-15 isoforms. J Immunol 158, 255-262.

PICKER, L. J., REED-INDERBITZIN, E. F., HAGEN, S. I., EDGAR, J. B., HANSEN, S. G., LEGASSE, A., PLANER, S. PIATAK, M, JR., LIFSON, J. D., MAINO, V. C., AXTHELM, M. K., and VILLINGER, F. (2006). IL-15 induces CD4 effector memory T cell production and tissue emigration in nonhuman primates. The Journal of clinical investigation 116, 1514-1524.

RAMANATHAN, M. P., CURLEY, E., 3RD, SU, M., CHAMBERS, J. A., and WEINER, D. B. (2002). Carboxyl terminus of hVIP/mov34 is critical for HIV-1-Vpr interaction and glucocorticoid-mediated signaling. The Journal of biological chemistry 277, 47854-47860.

SANDAU, M. M., SCHLUNS, K. S., LEFRANCOIS, L., and JAMESON, S. C. (2004). Cutting edge: transpresentation of IL-15 by bone marrow-derived cells necessitates expression of IL-15 and IL-15R alpha by the same cells. J Immunol 173, 6537-6541.

SATO, N., PATEL, H. J., WALDMANN, T. A., and TAGAYA, Y. (2007). The IL-15/IL-15Ralpha on cell surfaces enables sustained IL-15 activity and contributes to the long survival of CD8 memory T cells. Proceedings of the National Academy of Sciences of the United States of America 104, 588-593.

SCHLUNS, K. S., KLONOWSKI, K. D., and LEFRANCOIS, L. (2004a). Transregulation of memory CD8 T-cell proliferation by IL-15Ralpha+ bone marrow-derived cells. Blood 103, 988-994.

SCHLUNS, K. S., NOWAK, E. C., CABRERA-HERNANDEZ, A., PUDDINGTON, L., LEFRANCOIS, L., and AGUILA, H. L. (2004b). Distinct cell types control lymphoid subset development by means of IL-15 and IL-15 receptor alpha expression. Proceedings of the National Academy of Sciences of the United States of America 101, 5616-5621.

SCHMITZ, J. E., KURODA, M. J., SANTRA, S., SASSEVILLE, V. G., SIMON, M. A., LIFTON, M. A., RACZ, P., TENNER-RACZ, K., DALESANDRO, M., SCALLON, B. J., GHRAYEB, J., FORMAN, M. A., MONTEFIORI, D. C., RIEBER, E. P., LETVIN, N. L., and REIMANN, K. A. (1999). Control of viremia in simian immunodeficiency virus infection by CD8+ lymphocytes. Science (New York, N.Y. 283, 857-860.

SCHOENLY, K. A., and WEINER, D. B. (2008). Human immunodeficiency virus type 1 vaccine development: recent advances in the cytotoxic T-lymphocyte platform "spotty business". Journal of virology 82, 3166-3180.

SHIVER, J. W., FU, T. M., CHEN, L., CASIMIRO, D. R., DAVIES, M. E., EVANS, R. K., ZHANG, Z. Q., SIMON, A. J., TRIGONA, W. L., DUBEY, S. A., HUANG, L., HARRIS, V. A., LONG, R. S., LIANG, X., HANDT, L., SCHLEIF, W. A., ZHU, L., FREED, D. C., PERSAUD, N. V., GUAN, L., PUNT, K. S., TANG, A., CHEN, M., WILSON, K. A., COLLINS, K. B., HEIDECKER, G. J., FERNANDEZ, V. R., PERRY, H. C., JOYCE, J. G., GRIMM, K. M., COOK, J. C., KELLER, P. M., KRESOCK, D. S., MACH, H., TROUTMAN, R. D., ISOPI, L. A., WILLIAMS, D. M., XU, Z., BOHANNON, K. E., VOLKIN, D. B., MONTEFIORI, D. C., MIURA, A., KRIVULKA, G. R., LIFTON, M. A., KURODA, M. J., SCHMITZ, J. E., LETVIN, N. L., CAULFIELD, M. J., BETT, A. J., YOUIL, R., KASLOW, D. C., and EMINI, E. A. (2002). Replication-incompetent adenoviral vaccine vector elicits effective anti-immunodeficiency-virus immunity. Nature 415, 331-335.

SPRENT, J. (2003). Turnover of memory-phenotype CD8+ T cells. Microbes and infection/Institut Pasteur 5, 227-231.

TAGAYA, Y., BAMFORD, R. N., DEFILIPPIS, A. P., and WALDMANN, T. A. (1996). IL-15: a pleiotropic cytokine with diverse receptor/signaling pathways whose expression is controlled at multiple levels. Immunity 4, 329-336.

WALDMANN, T. (2002). The contrasting roles of IL-2 and IL-15 in the life and death of lymphocytes: implications for the immunotherapy of rheumatological diseases. Arthritis research 4 Suppl 3, S161-167.

WALDMANN, T. A., and TAGAYA, Y. (1999). The multifaceted regulation of interleukin-15 expression and the role of this cytokine in NK cell differentiation and host response to intracellular pathogens. Annual review of immunology 17, 19-49.

YAJIMA, T., NISHIMURA, H. ISHIMITSU, R., WATASE, T., BUSCH, D. H., PAMER, E. G., KUWANO, H., and YOSHIKAI, Y. (2002). Overexpression of IL-15 in vivo increases antigen-driven memory CD8+ T cells following a microbe exposure. J Immunol 168, 1198-1203.

ZHANG, W., DONG, S. F., SUN, S. H., WANG, Y., LI, G. D., and QU, D. (2006). Coimmunization with IL-15 plasmid enhances the longevity of CD8 T cells induced by DNA encoding hepatitis B virus core antigen. World J Gastroenterol 12, 4727-4735.

ZHANG, X., SUN, S., HWANG, I., TOUGH, D. F., and SPRENT, J. (1998). Potent and selective stimulation of memory-phenotype CD8+ T cells in vivo by IL-15. Immunity 8, 591-599.

---

The invention claimed is:
1. A nucleic acid molecule comprising SEQ ID NO: 1.
2. The nucleic acid molecule of claim 1, wherein the nucleic acid molecule is a plasmid.

* * * * *

SEQUENCE LISTING

<160> NUMBER OF SEQ ID NOS: 3

<210> SEQ ID NO 1
<211> LENGTH: 888
<212> TYPE: DNA
<213> ORGANISM: Artificial Sequence
<220> FEATURE:
<223> OTHER INFORMATION: Optimized IL-15 Receptor Alpha DNA Sequence

<400> SEQUENCE: 1

```
ggtaccggat ccgccaccat ggactggacc tggattctgt tcctggtggc tgccgccaca      60
agagtgcaca gcgcccccag gcgggccaga ggctgtagaa ccctgggcct gcctgctctg     120
ctgctgctgc tcctcctgag gcccctgcc accggggca tcacctgccc ccctcccatg     180
agcgtggagc acgccgacat ctgggtgaag agctacagcc tgtacagccg ggagcggtac     240
atctgcaaca gcggcttcaa gcggaaggcc ggcaccagca gcctgaccga gtgcgtgctg     300
aacaaggcca ccaacgtggc ccactggacc accccagcc tgaagtgcat ccgggacccc     360
gccctggtgc atcagagacc cgcccctcct agcacagtga ccacagccgg cgtgacccc      420 cagcccgaga gcctctcccc cagcggcaaa gagcctgccg ccagcagccc cagcagcaac     480
aacaccgccg ccacaaccgc cgccatcgtg cccggcagcc agctgatgcc cagcaagagc     540
ccttccaccg gcacaaccga gatcagcagc cacgagagca gccacggaaac accctctcag     600
```

```
accaccgcca agacctggga gctgaccgcc agcgcctctc accagcctcc tggcgtgtac    660
cctcagggcc acagcgacac caccgtggcc atcagcacct ccaccgtgct gctgtgcggc    720
ctgagcgccg tgagcctgct ggcctgctac ctgaagagcc ggcagacccc ccctctggcc    780
agcgtggaga tggaagctat ggaagccctg cctgtcacct ggggcaccag ctccagggac    840
gaggacctgg aaaactgcag ccaccacctg tgatgagaat tcgagctc                 888

<210> SEQ ID NO 2
<211> LENGTH: 855
<212> TYPE: DNA
<213> ORGANISM: Artificial Sequence
<220> FEATURE:
<223> OTHER INFORMATION: Non-optimized IL-15 Receptor Alpha Sequence

<400> SEQUENCE: 2
atggattgga cttggatctt attttttagtt gctgctgcta ctagagttca ttctgccccg     60
cggcgggcgc gcggctgccg gaccctcggt ctcccggcgc tgctactgct gctgctgctc    120
cggccgccgg cgacgcgggg catcacgtgc cctcccccca tgtccgtgga cacgcagac    180 atctgggtca agagctacag cttgtactcc agggagcggt acatttgtaa ctctggtttc    240
aagcgtaaag ccggcacgtc cagcctgacg gagtgcgtgt tgaacaaggc cacgaatgtc    300
gcccactgga caaccccccag tctcaaatgc attagagacc ctgccctggt tcaccaaagg    360
ccagcgccac cctccacagt aacgacggca ggggtgaccc cacagccaga gagcctctcc    420
ccttctggaa aagagcccgc agcttcatct cccagctcaa caacacagc ggccacaaca    480 gcagctattg tcccgggctc ccagctgatg ccttcaaaat caccttccac aggaaccaca    540
gagataagca gtcatgagtc ctcccacggc acccccctctc agacaacagc caagacctgg    600
gaactcacag catccgcctc ccaccagccg ccaggtgtgt atccacaggg ccacagcgac    660
accactgtgg ctatctccac gtccactgtc ctgctgtgtg ggctgagcgc tgtgtctctc    720
ctggcatgct acctcaagtc aaggcaaaact ccccgctgg ccagcgttga aatggaagcc    780
atggaggctc tgccggtgac ttgggggacc agcagcagag atgaagactt ggaaaactgc    840
tctcaccacc tatga                                                    855

<210> SEQ ID NO 3
<211> LENGTH: 3751
<212> TYPE: DNA
<213> ORGANISM: Artificial Sequence
<220> FEATURE:
<223> OTHER INFORMATION: Optimized IL-15 Receptor Alpha Sequence with an
      IgE leader

<400> SEQUENCE: 3
aaatgggggc gctgaggtct gcctcgtgaa gaaggtgttg ctgactcata ccaggcctga     60
atcgccccat catccagcca gaaagtgagg gagccacggt tgatgagagc tttgttgtag    120
gtggaccagt tggtgatttt gaacttttgc tttgccacgg aacggtctgc gttgtcggga    180
agatgcgtga tctgatcctt caactcagca aaagttcgat ttattcaaca aagccgccgt    240
cccgtcaagt cagcgtaatg ctctgccagt gttacaacca attaaccaat ctgcgttca    300 aaatggtatg cgttttgaca catccactat atatccgtgt cgttctgtcc actcctgaat    360
cccattccag aaattctcta gcgattccag aagtttctca gagtcggaaa gttgaccaga    420
cattacgaac tggcacagat ggtcataacc tgaaggaaga tctgattgct taactgcttc    480
agttaagacc gacgcgctcg tcgtataaca gatgcgatga tgcagaccaa tcaacatggc    540
```

```
acctgccatt gctacctgta cagtcaagga tggtagaaat gttgtcggtc cttgcacacg    600
aatattacgc catttgcctg catattcaaa cagctcttct acgataaggg cacaaatcgc    660
atcgtggaac gtttgggctt ctaccgattt agcagtttga tacactttct ctaagtatcc    720
acctgaatca taaatcggca aaatagagaa aaattgacca tgtgtaagcg gccaatctga    780
ttccacctga gatgcataat ctagtagaat ctcttcgcta tcaaaattca cttccacctt    840
ccactcaccg gttgtccatt catggctgaa ctctgcttcc tctgttgaca tgacacacat    900
catctcaata tccgaatacg gaccatcagt ctgacgacca agagagccat aaacaccaat    960
agccttaaca tcatccccat atttatccaa tattcgttcc ttaatttcat gaacaatctt   1020
cattctttct tctctagtca ttattattgg tccgttcata acaccccttg tattactgtt   1080
tatgtaagca gacagtttta ttgttcatga tgatatattt ttatcttgtg caatgtaaca   1140
tcagagattt tgagacacaa cgtggctttc cccggcccat gaccaaaatc ccttaacgtg   1200
agttttcgtt ccactgagcg tcagacccct agaaaagat caaaggatct tcttgagatc    1260 cttttttttct gcgcgtaatc tgctgcttgc aaacaaaaaa accaccgcta ccagcggtgg   1320
tttgtttgcc ggatcaagag ctaccaactc ttttttccgaa ggtaactggc ttcagcagag   1380
cgcagatacc aaatactgtt cttctagtgt agccgtagtt aggccaccac ttcaagaact   1440
ctgtagcacc gcctacatac ctcgctctgc taatcctgtt accagtggct gctgccagtg   1500
gcgataagtc gtgtcttacc gggttggact caagacgata gttaccggat aaggcgcagc   1560
ggtcgggctg aacggggggt tcgtgcacac agcccagctt ggagcgaacg acctacaccg   1620
aactgagata cctacagcgt gagctatgag aaagcgccac gcttcccgaa gggagaaagg   1680
cggacaggta tccggtaagc ggcagggtcg gaacaggaga gcgcacgagg gagcttccag   1740
ggggaaacgc ctggtatctt tatagtcctg tcgggtttcg ccacctctga cttgagcgtc   1800
gatttttgtg atgctcgtca ggggggcgga gcctatggaa aaacgccagc aacgcggcct   1860
ttttacggtt cctggccttt tgctggcctt ttgctcacat gttctttcct gcgttatccc   1920
ctgattctgt ggataaccgt attaccgcct ttgagtgagc tgataccgct cgccgcagcc   1980
gaacgaccga gcgcagcgag tcagtgagcg aggaagcgga agagcgcctg atgcggtatt   2040
ttctccttac gcatctgtgc ggtatttcac accgcatatg gtgcactctc agtacaatct   2100
gctctgatgc cgcatagtta agccagtatc tgctccctgc ttgtgtgttg gaggtcgctg   2160
agtagtgcgc gagcaaaatt taagctacaa caaggcaagg cttgaccgac aattgcatga   2220
agaatctgct tagggttagg cgttttgcgc tgcttcgcga tgtacgggcc agatatagcc   2280
gcggcatcga tgatatccat tgcatacgtt gtatctatat cataatatgt acatttatat   2340
tggctcatgt ccaatatgac cgccatgttg acattgatta ttgactagtt attaatagta   2400
atcaattacg gggtcattag ttcatagccc atatatggag ttccgcgtta cataacttac   2460
ggtaaatggc ccgcctggct gaccgcccaa cgacccccgc ccattgacgt caataatgac   2520
gtatgttccc atagtaacgc caatagggac tttccattga cgtcaatggg tggagtattt   2580
acggtaaact gcccacttgg cagtacatca agtgtatcat atgccaagtc cgccccctat   2640
tgacgtcaat gacggtaaat ggcccgcctg gcattatgcc cagtacatga ccttacggga   2700
ctttcctact tggcagtaca tctacgtatt agtcatcgct attaccatgg tgatgcggtt   2760
ttggcagtac atcaatgggc gtggatagcg gtttgactca cggggatttc caagtctcca   2820
ccccattgac gtcaatggga gtttgttttg gcaccaaaat caacgggact ttccaaaatg   2880
tcgtaacaac tccgccccat tgacgcaaat gggcggtagg cgtgtacggt gggaggtcta   2940
```

```
tataagcaga gctcgtttag tgaaccgtca gatcgcctgg agacgccatc cacgctgttt     3000
tgacctccat agaagacacc gggaccgatc cagcctccgc gggcgcgcgg tccagtgtgg     3060
tggaattcgc cgccaccatg gattggactt ggatcttatt tttagttgct gctgctacta     3120
gagttcattc taactgggtg aatgtaataa gtgatttgaa aaaaattgaa gatcttattc     3180
aatctatgca tattgatgct actttatata cggaaagtga tgttcacccc agttgcaaag     3240
taacagcaat gaagtgcttt ctcttggagt tacaagttat ttcacttgag tccggagatg     3300
caagtattca tgatacagta gaaaatctga tcatcctagc aaacaacagt ttgtcttcta     3360
atgggaatgt aacagaatct ggatgcaaag aatgtgagga actggaggaa aaaaatatta     3420
aagaattttt gcagagtttt gtacatattg tccaaatgtt catcaacact tcttgactcg     3480
gggcgacgcg aaacttgggc ccactcgaga ggcgcgccga gctcgctgat cagcctcgac     3540
tgtgccttct agttgccagc catctgttgt ttgcccctcc cccgtgcctt ccttgaccct     3600
ggaaggtgcc actcccactg tcctttccta ataaaatgag gaaattgcat cgcattgtct     3660
gagtaggtgt cattctattc tggggggtgg ggtggggcag gacagcaagg gggaggattg     3720
ggaagacaat agcaggcatg ctggggaatt t                                    3751
```